(12) United States Patent
Kim et al.

(10) Patent No.: US 7,771,964 B2
(45) Date of Patent: Aug. 10, 2010

(54) METHOD OF OVERPRODUCTION OF POLYHYDROXYBUTYRATE

(75) Inventors: In Gyu Kim, Taejon (KR); Il Lae Jung, Taejon (KR); Hyo Kook Park, Taejon (KR); Kug Chan Kim, Taejon (KR); Byung Ho Choi, Taejon (KR)

(73) Assignee: Korea Atomic Energy Research Institute, Taejon (KR)

( * ) Notice: Subject to any disclaimer, the term of this patent is extended or adjusted under 35 U.S.C. 154(b) by 0 days.

(21) Appl. No.: 10/998,473

(22) Filed: Nov. 29, 2004

(65) Prior Publication Data

US 2005/0227340 A1 Oct. 13, 2005

(30) Foreign Application Priority Data

Apr. 8, 2004 (KR) ................... 10-2004-0024154

(51) Int. Cl.
*C12P 1/00* (2006.01)
*C12P 7/00* (2006.01)
*C12P 7/02* (2006.01)
*C12P 7/18* (2006.01)

(52) U.S. Cl. ................... 435/41; 435/132; 435/155; 435/158

(58) Field of Classification Search ................... 435/135
See application file for complete search history.

(56) References Cited

OTHER PUBLICATIONS

Wang et al., Appl. Environ. Microbiol. Sep. 1997;63(12):4765-4769.*
Ngo et al. In the Protein Folding Problem and Tertiary Structure Prediction, 1994, Merz et al. (ed.), Birkhauser, Boston, MA, pp. 433 and 492-495.*
Belo et al., Batch and fed-batch cultures of *E.coli* TB1 at different oxygen transfer rates, Bioprocess Engineering, 1998, 18: 451-455.*
*E. coli* Statistics [online], Retrieved from the Internet <URL: http://redpoll.pharmacy.ualberta.ca/CCDB/cgi-bin/STAT_NEW.cgi>.*
The Qiagen Guide to Good Microbiological Practice, Issue No. 5, 1998, [online] Retrieved from the Internet <URL: http://www.qiagen.com>.*
Chou et al. Biotechnology and Bioengineering 47:186-192, 1995.*
Bunch et al. (The IdhA gene encoding the fermentative lactate dehydrogenase of *Escherichia coli*, Microbiology (1997), 143, 187-195).*
Sigma-Aldrich catalog, Retrieved from the Internet <URL:http://www.sigmaaldrich.com/catalog/ProductDetail.do?lang=en&N4=L2542|SIGMA&N5=SEARCH_CONCAT_PNO|BRAND_KEY&F=SPEC>, Sep. 22, 2009.*
Skandamis et al. (Modeling the effect of inoculum size and acid adaptation on growth/no growth interface of *Escherichia coli* O157:H7, International Journal of Food Microbiology, 120, (2007), 237-249).*
Schubert, Peter, et al., Cloning of the *Alcaligenese Eutrophus* Genes for Synthesis of . . . , Journal of Bacteriology, vol. 170,No. 12, pp. 5837-5847, (1988).
Sang Yup Lee, et al., Production of Poly(B-Hydroxybutyric Acid) by Recombinant *Escherichia coli*, Annals New York Academy of Sciences, (1994).
J.A. Ramsay, et al., Extraction of Poly-3-Hydroxybutyrate Using Chlorinated Solvents, Biotechnology Techniques, vol. 8, No. 8, pp. 589-594 (1994).
Tsuneo Yamane, et al., Increased PHB Productivity by High-Cell-Density Fed-Batch Culture of *Alcaligenes latus*, a Growth-Associated PHB Producer, Biotechnology and Bioengineering, vol. 50, pp. 197-202 (1996).
T. Hai, et al., Multiple Evidence for Widespread and General Occurrence of Type-III PHA Synthases in Cyanobacteria . . . , Microbiology, vol. 147 pp. 3047-3060 (2001).
Resch, S., Aqueous release and purfication of poly($\beta$-hydrozbutyrate) from *Escherichia coli*, Journal of Biotechnology, 1998, vol. 65, pp. 173-182.

* cited by examiner

*Primary Examiner*—David J Steadman
*Assistant Examiner*—Jae W Lee
(74) *Attorney, Agent, or Firm*—Lucas & Mercanti, LLP

(57) ABSTRACT

The present invention relates to a recombinant *Escherichia coli* having phbCAB originated from *Alcaligenes eutrophus* and an overproduction method of polyhydroxyalkanoate using the same, more precisely, a recombinant *Escherichia coli* 'MG1655/pTZ18U-PHB' or 'JIL938/pTZ18U-PHB' having phbCAB originated from *Alcaligenes eutrophus* and an overproduction method of polyhydroxyalkanoate comprising the steps of preparing transformed *Escherichia coli* having phbCAB originated from *Alcaligenes eutrophus*, inoculating and culturing the cells (growth phase), inducing the production of polyhydroxyalkanoate in the recomibnant *Escherichia coli* (stationary phase and producing phase), and inducing the extracellular secretion of the polyhydroxyalkanoate from the recombinant *Escherichia coli*. The method of the present invention facilitates not only overproduction of polyhydroxyalkanoate such as polyhydroxybutyrate by a simple batch culture but also industrial use of biodegradable polyhydroxyalkanoate replacing conventional non-biodegradable plastics by its simple and easy fermentation, separation and purification process.

12 Claims, 28 Drawing Sheets

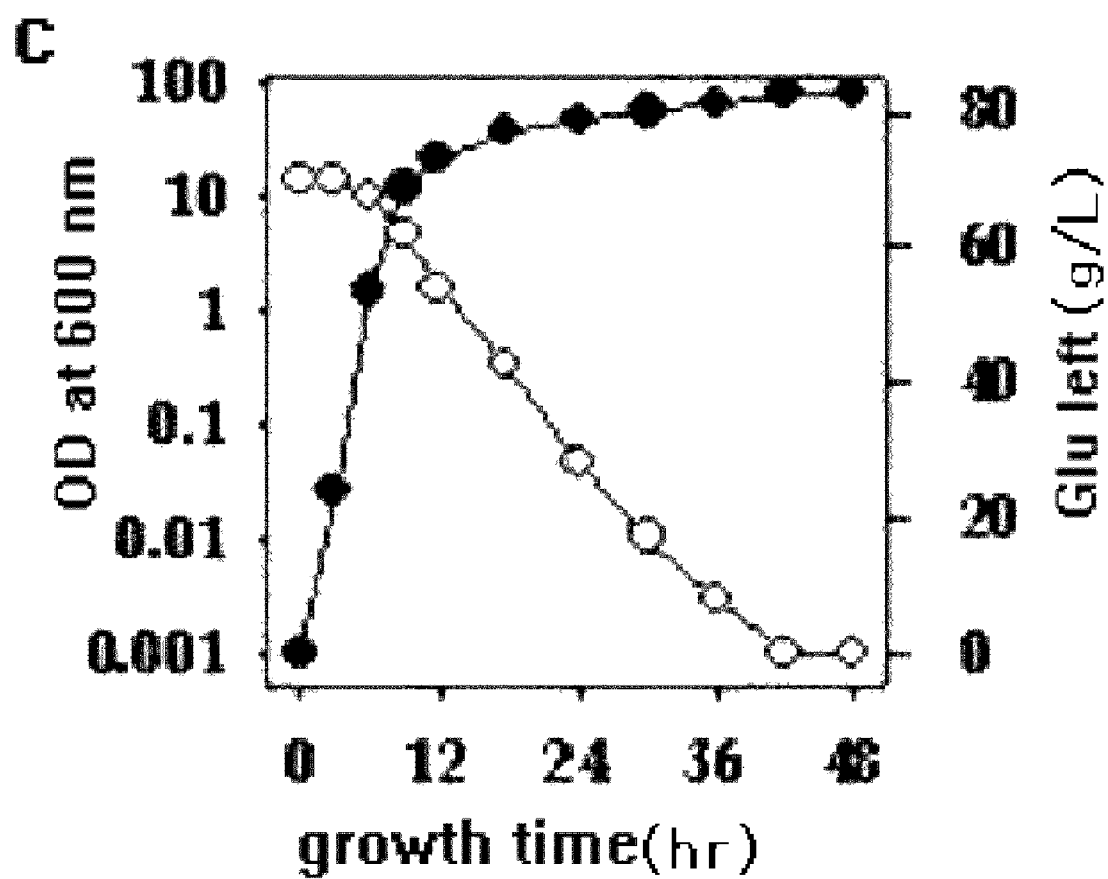

SEQUENCE LISTING

<160> NUMBER OF SEQ ID NOS: 3

<210> SEQ ID NO 1
<211> LENGTH: 1770
<212> TYPE: DNA
<213> ORGANISM: Alcaligenes eutrophus

<400> SEQUENCE: 1

```
atggcgaccg gcaaaggcgc ggcagcttcc acgcaggaag gcaagtccca accattcaag      60
gtcacgccgg ggccattcga tccagccaca tggctggaat ggtcccgcca gtggcagggc     120
actgaaggca acgccacgc ggccgcgtcc ggcattccgg gcctggatgc gctggcaggc     180
gtcaagatcg cgccggcgca gctgggtgat atccagcagc gctacatgaa ggacttctca     240
gcgctgtggc aggccatggc cgagggcaag gccgaggcca ccggtccgct gcacgaccgg     300
cgcttcgccg gcgacgcatg gcgcaccaac ctcccatatc gcttcgctgc cgcgttctac     360
ctgctcaatg cgccgcgcctt gaccgagctg gccgatgccg tcgaggccga tgccaagacc     420
cgccagcgca tccgcttcgc gatctcgcaa tgggtcgatg cgatgtcgcc cgccaacttc     480
cttgccacca atcccgaggc gcagcgcctg ctgatcgagt cgggcggcga atcgctgcgt     540
gccggcgtgc gcaacatgat ggaagacctg acacgcggca agatctcgca gaccgacgag     600
agcgcgtttg aggtcggccg caatgtcgcg gtgaccgaag gcgccgtggt cttcgagaac     660
gagtacttcc agctgttgca gtacaagccg ctgaccgaca aggtgcacgc gcgcccgctg     720
ctgatggtgc cgccgtgcat caacaagtac tacatcctgg acctgcagcc ggagagctcg     780
ctggtgcgcc atgtggtgga gcagggacat acggtgtttc tggtgtcgtg gcgcaatccg     840
gacgccagca tggccggcag cacctgggac gactacatcg agcacgcggc catccgcgcc     900
atcgaagtcg cgcgcgacat cagcggccag gacaagatca acgtgctcgg cttctgcgtg     960
ggcggcacca ttgtctcgac cgcgctggcg gtgctggccg cgcgcggcga gcacccggcc    1020
gccagcgtca cgctgctgac cacgctgctg gactttgccg acacgggcat cctcgacgtc    1080
tttgtcgacg agggccatgt gcagttgcgc gaggccacgc tgggcggcgg cgccggcgcg    1140
ccgtgcgcgc tgctgcgcgg ccttgagctg gccaatacct tctcgttctt gcgcccgaac    1200
gacctggtgt ggaactacgt ggtcgacaac tacctgaagg gcaacacgcc ggtgccgttc    1260
gacctgctgt tctggaacgg cgacgccacc aacctgccgg ggccgtggta ctgctggtac    1320
ctgcgccaca cctacctgca gaacgagctc aaggtaccgg gcaagctgac cgtgtgcggc    1380
```

-continued

```
gtgccggtgg aacctggccag catcgacgtg ccgacctata tctacggctc gcgcgaagac    1440
catatcgtgc cgtggaccgc ggcctatgcc tcgaccgcgc tgctggcgaa caagctgcgc    1500
ttcgtgctgg gtgcgtcggg ccatatcgcc ggtgtgatca acccgccggc caagaacaag    1560
cgcagccact ggactaacga tgcgctgccg gagtcgccgc agcaatggct ggccggcgcc    1620
atcgagcatc acggcagctg gtggccggac tggaccgcat ggctgccgg gcaggccggc    1680 gcgaaacgcg ccgcgcccgc caactatggc aatgcgcgct atcgcgcaat cgaacccgcg    1740
cctgggcgat acgtcaaagc caaggcatga                                     1770
```

<210> SEQ ID NO 2
<211> LENGTH: 1181
<212> TYPE: DNA
<213> ORGANISM: Alcaligenes eutrophus

<400> SEQUENCE: 2

```
atgactgacg ttgtcatcgt atccgccgcc cgcaccgcgg tcggcaagtt tggcggctcg     60
ctggccaaga tcccggcacc ggaactgggt gccgtggtca tcaaggccgc gctggagcgc    120
gccggcgtca agccggagca ggtgagcgaa gtcatcatgg gccaggtgct gaccgccggt    180
tcgggccaga accccgcacg ccaggccgcg atcaaggccg gctgccggc gatggtgccg    240 gccatgacca tcaacaaggt gtgcggctcg ggcctgaagg ccgtgatgct ggccgccaac    300
gcgatcatgg cgggcgacgc cgagatcgtg gtggccggcg gccaggaaaa catgagcgcc    360
gccccgcacg tgctgccggg ctcgcgcgat ggtttccgca tgggcgatgc caagctggtc    420
gacaccatga tcgtcgacgg cctgtgggac gtgtacaacc agtaccacat gggcatcacc    480
gccgagaacg tggccaagga atacggcatc acacgcgagg cgcaggatga gttcgccgtc    540
ggctcgcaga acaaggccga agccgcgcag aaggccggca gtttgacga agagatcgtc    600 ccggtgctga tcccgcagcg caagggcgac ccggtggcct tcaagaccga cgagttcgtg    660
cgccagggcg ccacgctgga cagcatgtcc ggcctcaagc ccgccttcga caaggccggc    720
acggtgaccg cggccaacgc ctcgggcctg aacgacggcg ccgccgcggt ggtggtgatg    780
tcggcggcca aggccaagga actgggcctg accccgctgg ccacgatcaa gagctatgcc    840
aacgccggtg tcgatcccaa ggtgatgggc atgggcccgg tgccggcctc caagcgcgcc    900
ctgtcgcgcg ccgagtggac cgcaagacc tggacctgat ggagatcaac gaggcctttg    960
ccgcgcaggc gctggcggtg caccagcaga tgggctggga cacctccaag gtcaatgtga   1020
acggcggcgc catcgccatc ggccacccga tcggcgcgtc gggctgccgt atcctggtga   1080
cgctgctgca cgagatgaag cgccgtgacg cgaagaaggg cctggcctcg ctgtgcatcg   1140
gcggcggcat gggcgtggcg ctggcagtcg agcgcaaata a                       1181
```

<210> SEQ ID NO 3
<211> LENGTH: 741
<212> TYPE: DNA
<213> ORGANISM: Alcaligenes eutrophus

<400> SEQUENCE: 3

```
atgactcagc gcattgcgta tgtgaccggc ggcatggggt gtatcggaac cgccatttgc     60
cagcggctgg ccaaggatgg ctttcgtgtg gtggccggtt gcggcccaa ctcgccgcgc    120 cgcgaaaagt ggctggagca gcagaaggcc ctgggcttcg atttcattgc ctcggaaggc    180
aatgtggctg actgggactc gaccaagacc gcattcgaca aggtcaagtc cgaggtcggc    240
```

```
-continued gaggttgatg tgctgatcaa caacgccggt atcacccgcg acgtggtgtt ccgcaagatg    300
acccgcgccg actgggatgc ggtgatcgac accaacctga cctcgctgtt caacgtcacc    360
aagcaggtga tcgacggcat ggccgaccgt ggctggggcc gcatcgtcaa catctcgtcg    420
gtgaacgggc agaagggcca gttcggccag accaactact ccaccgccaa ggccggcctg    480
catggcttca ccatggcact ggcgcaggaa gtggcgacca agggcgtgac cgtcaacacg    540
gtctctccgg gctatatcgc caccgacatg gtcaaggcga tccgccagga cgtgctcgac    600
aagatcgtcg cgacgatccc ggtcaagcgc ctgggcctgc cggaagagat cgcctcgatc    660
tgcgcctggt tgtcgtcgga ggagtccggt ttctcgaccg gcgccgactt ctcgctcaac    720
ggcggcctgc atatgggctg a                                              741
```

METHOD OF OVERPRODUCTION OF POLYHYDROXYBUTYRATE

This patent application claims the benefit of priority from Korean Patent Application No. 10-2004-0024156 filed Apr. 8, 2004, the contents of which are incorporated herein by reference.

FIELD OF THE INVENTION

The present invention relates to a recombinant *Escherichia coli* and an overproduction method of polyhydroxyalkanoate using the same, more precisely, a recombinant *Escherichia coli* having phbCAB originated from *Alcaligenes eutrophus* and an overproduction method of polyhydroxyalkanoate using the same.

BACKGROUND

Although petroleum-derived non-biodegradable plastics have been indispensable materials in modern society over the past several decades and have enabled human beings to live in more comfortable circumstances, the increasing plastic wastes have been severe environmental contaminants causing waste disposal problems and even a threat to human. In an effort to prevent the harmful environmental effects of non-biodegradable plastics, the development of environmental-friendly biodegradable plastics has been going on all over the world.

Microorganism-derived biodegradable plastics have a number of advantages over conventional petroleum-derived plastics. They are biodegradable, biocompatible and biologically renewable, making them as useful candidates for replacing conventional synthetic plastics (Steinbuchel, A. and Fuchtenbusch, B., *Appl. Microbiol. Biotechnol.*, 51: 13-21, 1999; Poirier, Y., *Curr. Opin. Biotechnol.*, 10; 181-185, 1999). Target markets for biodegradable plastics include packaging materials, disposable fabrics, hygiene products, consumer goods, agricultural tools, fine chemistry, and other disposables, which are being enlarged with increase of consumption (Gross, R, A, and Kalra, B., *Science*, 297: 803-807, 2002).

Polyhydroxyalkanoates (PHAs) derived from microorganisms have drawn much attention as candidates for manufacturing natural and biodegradable thermoplastics and elastomers for a wide range of applications, because they are degraded completely to $CO_2$ and $H_2O$ under optimal conditions and they possess material properties similar to various petrochemical-based synthetic plastics currently in use (Holmes, P. A., *Phyl. Technol.*, 16: 32-36, 1985; Lee, S Y. *Biotechnol. Bioeng.*, 49: 1-14, 1996). Although a company (Metabolix, USA) sells PHA under the trade name of BIOPOL, the use of PHA is limited because of its high production cost (Choi, J. and Lee, S Y. *Appl. Microbiol. Biotechnol.*, 51: 13-21, 1999).

When PHA is produced in bacterial fermentation systems, the unit cost of production is at least five times higher than that of chemically synthesized polyethylene. Therefore, the use of microorganism-derived PHA is limited to a narrow range just because of high production price. Although the potential for such biodegradable plastics is great, they cannot compete with conventional petroleum-based plastics in production cost, so that the use of biodegradable plastics is limited to special applications (Choi, J. and Lee, S Y., *Appl. Microbiol Biotechnol.*, 51: 13-21, 1999; Lee, S Y., *Nature Biotechnol.*, 15: 17-18, 1997). In order to commercialize PHA, every effort has been made to reduce production price by the development of better host strains, improved fermentation processes and more efficient purification processes (Choi, J. and Lee, S. Y., *Appl. Microbiol. Biotechnol.*, 51: 13-21, 1999).

Polyhydroxybutyrate (PHB) is accumulated as a carbon and energy storage material in various microorganisms and is the best-characterized member of the polyhydroxyalkanoates (PHAs), which have drawn much attention as biodegradable substitutes for conventional nonbiodegradable plastics. It belongs to a class of polyesters of 3-hydroxy acids and has physical properties similar to those of polypropylene (Schubert, P. et al., *J. Bacteriol.*, 170: 5837-5847, 1998; Hai, T. et al., *Microbiology*, 147: 3047-3060, 2001; Anderson, A. J. and Dawes, E. A., *Microbiol. Rev.*, 54: 450-472, 1990; Lee, S Y., *Nature Biotechnol.*, 15: 17-18, 1997). PHB is derived from acetyl-coenzyme A by a sequence of three consecutive enzymatic reactions (Schubert, P. et al., *J. Bacteriol.*, 170: 5837-5847, 1988; Slater, S. C. et al., *J. Bacteriol.*, 170: 4431-4436, 1988). Polymerization of two molecules of acetyl-CoA is catalyzed by β-ketothiolase to form acetoacetyl-CoA. Then, acetyl-CoA reductase reduces acetoacetyl-CoA to β-hydroxybutyryl-CoA, which is then polymerized by PHB synthase to PHB. Three genes involved in the synthesis of PHB have been cloned from *Alcaligenes eutrophus* (Schubert, P. et al., *J. Bacteriol.*, 170: 5837-5847, 1988; Peoples, O. P. and Sinskey, A. J., *J. Biol. Chem.*, 264: 15298-15303, 1989; Slater, S. C. et al., *J. Bacteriol.*, 170: 4431-4436, 1988).

Various host strains have been investigated as candidates for the production of PHA. Among them, *A. eutrophus*, *A. latus*, methylotroph, *Azotobacter vinelandii*, and recombinant *Escherichia coli* are considered to be good PHA producers (Lee, S Y., *Biotechnol. Bioeng.*, 49: 1-14, 1996; Lee, S Y., *Trends Biotechnol.*, 14: 431-438, 1996; Lee, S Y., *Nature Biotechnol.*, 15: 17-18, 1997). In particular, production of PHB by recombinant *E. coli* having PHA synthesis gene derived from *A. eutrophus* has been studied by several groups (Fidler, S. and Dennis, D., *FEMS Microbiol. Rev.*, 9: 231-235, 1992; Lee, SY. et al., *Ann. N.Y. Acad. Sci.*, 721: 43-53, 1994; Lee, SY. et al., *Biotechnol. Bioeng.*, 44: 1337-1347, 1994). In addition, several groups have developed fermentation processes to increase productivity and these efforts are still largely ongoing. It has been reported that a high concentration of PHB can be produced with high productivity by a fed-batch culture of recombinant *E. coli* harboring a stable high copy number plasmid which carries phbCAB genes and content greater than 80% of dry cell weight (DCW) (Lee, SY., *Nature Biotechnol.*, 15: 17-18, 1997; Wang, F. and Lee, S Y., *Appl. Environ. Microbiol.*, 63: 4765-4769, 1997).

A number of PHA recovery/purification methods have been suggested. Although extraction using solvents such as chloroform, methylene chloride, and dichloroethane can result in pure PHA, this method requires large quantities of toxic and volatile solvents, causing additional environmental problems (Ramsay, J. A. et al., *Biotech. Tech.*, 8: 58-9-594, 1994; Choi, J. and Lee, S Y., *Bioprocess Eng.*, 17: 335-342, 1997). The recovery cost is considerably decreased with increasing PHA content (P/X, %). Lower PHA content, though, results in a higher recovery cost mainly due to the use of a larger amount of digesting agents for separating PHA and the increased cost of waste disposal (Lee, S Y. and Choi J., *Polymer Degrad. Stabil.*, 59: 387-393, 1998).

In addition to the factors described above, finding cheaper carbon sources has also been considered to be important because the cost of the carbon source also contributes significantly to the overall production cost of PHA (Yamane, T. et al., *Biotechnol. Bioeng.*, 50: 197-202, 1996; Yamane, T., *Biotechnol. Bioeng.*, 41: 165-170, 1993). In addition, carbon conversion rate is an important factor affecting the overall production cost. The goal is to have the carbon be 100% converted to PHB, resulting in the maximum possible glucose conversion rate (theoretical value of 0.38).

PHB is accumulated as a cell storage material in microorganisms, making it a useful candidate for a biodegradable plastic replacing conventional petroleum-based plastics. However, its use is limited to a narrow range of industrial applications because of high production cost, which makes it not compare favorably with conventional petroleum-based plastics. Various approaches to producing PHB on a commercial scale have been made. Nevertheless, commercial production of PHB remains distant, because production cost of PHB is still 4-5 times higher than that of synthetic plastics currently in use.

After all the researches on production of PHB, the present inventors have confirmed that PHB production could be effectively induced by inhibiting generation of lactate in cells by initial low inoculum. And the present inventors have completed this invention with the development of a method for over-production of PHB on a commercial scale, in which necessary medium components are provided double for high productivity of PHB, production of PHB on an industrial scale is increased by adding high concentration of glucose, the concentration of PHB in a host cell is absolutely increased and extracellular secretion of PHB is induced to simplify PHB recovery/purification process, resulting in the decrease of production cost of PHB.

SUMMARY OF THE INVENTION

It is an object of this invention to provide a recombinant *Escherichia coli* having phbCAB originated from *Alcaligenes eutrophus*.

It is also an object of this invention to provide an over-production method of PHB on a commercial scale by a simple batch culture, by which PHB can compete with conventional synthetic plastics with lowered production cost and negative factors obstructing industrial mass-production of PHB are overcome.

DETAILED DESCRIPTION OF PREFERRED EMBODIMENTS

In order to achieve the above object, the present invention provides a recombinant *Escherichia coli* MG1655/pTZ18U-PHB or JIL938/pTZ18U-PHB having phbCAB originated from *Alcaligenes eutrophus*.

The present invention also provides an over-production method of polyhydroxyalkanoate comprising the steps of preparing a recombinant *E. coli* harboring phbCAB gene derived from *Alcaligenes eutrophus*; inoculating (less than $10^5$ cells/1 ml of LB medium) and culturing the cells (growth phase); inducing the production of polyhydroxyalkanoate in the recombinant *Escherichia coli* (stationary phase and producing phase); and inducing the extracellular secretion of the polyhydroxyalkanoate from the recombinant *Escherichia coli*.

The present invention further provides a method for keeping PHB being produced in cells highly and stably with initial low inoculum. In addition, the present invention provides a way to simplify the troublesome efforts to regulate a carbon source for fermentation by enabling PHB production with high concentration of glucose. The present invention also provides a method for over-production of PHB, in which necessary medium components are provided double to increase PHB productivity.

At last, the present invention provides a method to simplify PHB recovery/purification process by increasing the concentration of PHB in cells greatly, attributed to the production of non-growth dependent PHB.

Hereinafter, the present invention is described in detail.

The present invention provides a recombinant *Escherichia coli* MG1655/pTZ18U-PHB or JIL938/pTZ18U-PHB having phbCAB originated from *Alcaligenes eutrophus*.

MG 1655 strain, a member of *E. coli* K-12, is a wild type strain and JIL938 is prepared by mutating ldh gene of MG1655 strain. SE1752 (ldh::Tn10) was infected with bacteriophage P1vir, resulting in P1 (ldh:Tn10). Mother strain MG1655 was re-infected with P1 (ldh:Tn10), which was inoculated on LB/tetracycline solid medium. The growing strain on the medium was selected for the preparation of JIL938.

The present invention also provides an over-production method of polyhydroxyalkanoate comprising the steps of preparing a recombinant *E. coli* harboring phbCAB gene derived from *Alcaligenes eutrophus*; inoculating (less than $10^5$ cells/1 ml of LB medium) and culturing the cells (growth phase); inducing the production of polyhydroxyalkanoate in the recombinant *Escherichia coli* (stationary phase and producing phase); and inducing the extracellular secretion of the polyhydroxyalkanoate from the recombinant *Escherichia coli*.

The LB medium above was preferably composed of Bacto tryptone, Bacto-yeast extract and NaCl.

PHB was synthesized by a sequence of three consecutive enzymatic reactions of phbCAB gene derived from *A. eutrophus*. MG1655 strain (wild type *E. coli* strain) was transformed with pTZ18U-PHB plasmid containing the gene, resulting in a recombinant host strain. The recombinant *E. coli* strain was cultured in a complex medium LB/glucose/amp, during which PHB was accumulated when initial inoculum size was smaller than $10^5$ cells/ml and better accumulated when initial inoculum size was smaller than $2 \times 10^4$ cells/ml.

In the present invention, PHB accumulation was shown 4 hours after inoculating the LB/glucose/amp medium with high concentration of cells, but PHB accumulation did not progressed any more even though the culture was continued. When the medium was inoculated with low concentration of cells ($10^4$ cells/ml), PHB accumulation was shown 6 hours later and the size of accumulated intracellular granules was increased stably as culture went on further.

In this invention, among phbCAB genes, phbC gene is preferred to be abase sequence represented by SEQ ID NO: 1, phbA gene is preferred to be a base sequence represented by SEQ ID NO: 2, phbB gene is preferred to be a base sequence represented by SEQ ID NO: 3, and the whole phbCAB gene is preferred to be a base sequence represented by SEQ ID NO 1, SEQ ID NO: 2 and SEQ ID NO: 3 in the order given.

It is also preferred to use pTZ18U-PHB plasmid harboring the above phbCAB gene. And a recombinant *E. coli* strain in the present invention is preferred to be MG1655/pTZ18U-PHB or a strain having mutated ldh gene, and more preferred to be JIL938/pTZ18U-PHB.

The preferable inoculum size for cell growth, in the present invention, is less than $2 \times 10^4$ cells/1 ml of LB medium.

It is preferred to add glucose in stationary phase and in producing phase instead of adding in LB medium of growth phase. In case glucose should be added in LB medium of growth phase, the preferable glucose concentration is less than 10% and 7% is more preferable. The preferable composition for the above LB medium includes glucose/ampicillin under LB/7%.

In the present invention, PHA is polyhydroxybutyrate (PHB).

LB medium of the present invention is preferably composed of over 10 g of Bacto tryptone, over 5 g of Bacto-yeast extract and over 10 g of NaCl per 1 l of the medium. If narrowing the range preferably, the composition includes 10-20 g of Bacto-trypton, 5-10 g of Bacto-yeast extract and 10-20 g of NaCl per 1 l of LB medium, and additionally has glucose less than 21%.

In the preferred embodiment of the present invention, pTZ18U-PHB plasmid harboring phbCAB gene derived from *A. eutrophus* was inserted into an *E. coli* strain to prepare a recombinant *E. coli* host strain. The recombinant *E. coli* strain was cultured in LB medium to be prepared as an inoculum. Cultivation of the inoculum was performed with low inoculum size and high inoculum size, respectively, resulting in difference in the form of colony and huge PHB generation only with low inoculum size (see FIGS. 1*a*, 1*b* and 1*c*).

In the preferred embodiment of the present invention, cell number did not increase further after 6 hour of cultivation of a recombinant *E. coli* strain, following inoculation with a low inoculum size, but OD was continuously increased. PHB accumulation, according to low or high inoculum size, was also investigated. As a result, the lower the inoculum size, the higher the OD value and the more PHB was produced. That is, intracellular PHB was stably accumulated with a low inoculum size and the size of PHB granules increased according to culture time (see FIGS. 2 and 3).

In order to confirm the importance of a low inoculum size, PHB synthesis was investigated under different conditions. In order to achieve this goal, culture solution after 8 hour of cultivation, in which no more cells were increased, and the cells cultured for 8 hours were investigated. As a result, cells cultured for 8 hours after inoculation with a low inoculum size acted as an important factor for a large amount of PHB production, regardless of medium condition. On the contrary, cells cultured for 8 hours after inoculation with a high inoculum size lost their ability to produce PHB. OD was also measured to investigate cell growth. In an early stage of cultivation, a high inoculum size accelerated cell growth, but after a certain point of time, OD was increased with a low inoculum size, which seemed to be due to the accumulation of PHB (see FIGS. 4*a*, 4*b* and 4*c*). Therefore, it has been confirmed that PHB accumulation is attributed to cells themselves, suggesting that "capable" cells act as an important factor for PHB accumulation and can be secured by cultivation with a low inoculum size. That is, "capable" cells can produce PHB effectively, regardless of medium conditions.

In the preferred embodiment of the present invention, in order to find out a reason for high concentration of PHB accumulation with a low inoculum size, PHB and competitive lactate pathways were investigated to examine lactate production. Precisely, pyruvate, a precursor for PHB production, acts as a branch point for the pathways for PHB and lactate production. When a high inoculum size was applied, lactate production was twice as much as when a low inoculum size was applied (see Table 1). Whether lactate production had negative effect on PHB synthesis was also investigated, for which a new strain without ldh gene involved in lactate production was prepared and inserted with pTZ18U-PHB plasmid, resulting in a novel recombinant strain. The high concentration of PHB accumulation was shown in the ldh recombinant strain, regardless of initial inoculum size, suggesting that lactate production pathway had a negative effect on PHB production (see FIG. 5).

In the preferred embodiment of the present invention, non-growth dependent PHB production was investigated, on completing the cultivation, to explain the increase of OD by the increase of the size of granules without increasing of cell numbers (see FIG. 4*b*).

In order to confirm if PHB production was growth-dependent or non-growth dependent, a novel plasmid 'pPHB-n' not containing a normal phbCAB gene was prepared, and a recombinant *E. coli* harboring a normal phbCAB gene and the other deficient in phbCAB gene were prepared for cultivation (see FIG. 6*a*) Glucose was provided during the culture of recombinant *E. coli* carrying a normal phbCAB gene, from which PHB accumulation was confirmed to be non-growth dependent at the late stage of cell growth, regardless of inoculum size (see FIGS. 6*b* and 6*c*) Besides, it was confirmed that it is important for cells to obtain the capability of PHB production in early growth times (see FIG. 6*d*).

In order to determine optimum glucose concentration, the present inventors compared coefficient of glucose utilization in different media supplemented with various glucose concentrations, in which recombinant *E. coli* cells were growing, and PHB productions therein, too (see FIGS. 7*a* and 7*b*). Other factors affecting PHB production cost, when a required concentration of glucose was given, were also investigated (see FIG. 7*c*, 7*d*, 7*e* and 7*f*). In addition, autolysis was measured, and PHB accumulation, according to culture time, was observed under optical microscope (see FIG. 8). As a result, intracellular PHB granules were increased in proportion to culture time, leading to autolysis outside cells.

In the preferred embodiment of the present invention, a complex medium having a high concentration, in which glucose was additionally included and other shortages were supplemented, was used, aiming at enabling mass-production of PHB on an industrial but laboratory scale. When 2×LB was used, OD, glucose consumption and the size of granules, in addition to PHB content in cells, were all increased greatly, comparing to when 1×LB was used (see FIG. 9*a*, 9*b*, 9*c* and 9*d*). From the observation under optical microscope, cells cultured in 2×LB medium were bigger and PHB concentrations in those cells were higher, after glucose supplementation, than those cultured in 1×LB medium (see FIG. 10*a*, 10*b* and 10*c*), which were also confirmed by the observations under scanning electron microscope (SEM) and transmission electron microscope (TEM) (see FIGS. 11, 12*a* and 12*b*).

In order to investigate if the accumulated PHB could effectively be recovered and purified, cell culture solution was treated simply by distilled water to test easiness of purification process.

The production method of the present invention facilitates an industrial use of PHB by dealing with various factors affecting PHB production cost. Therefore, the present invention contributes to facilitate over-production of PHB on a commercial scale by simplifying culture processes and enhancing purification processes. In addition, the method of the present invention can equally be applied to the treatment of copolymer. Thus, the method of the present invention can effectively be used not only for the production of various biodegradable plastics including PHB but also for the development of copolymers and for the commercial use of the same.

BRIEF DESCRIPTION OF THE DRAWINGS

The application of the preferred embodiments of the present invention is best understood with reference to the accompanying drawings, wherein.

●, no Glc: MG1655/pTZ18U-PHB cells were inoculated in LB/amp liquid medium without glucose with a low inoculum size ($10^4$ cells/ml), ○, Glc: MG1655/pTZ18U-PHB cells were inoculated in LB/amp liquid medium with a low inoculum size ($10^4$ cells/ml). 8 hr later, glucose 7% was added to the culture.

Figure 6A:
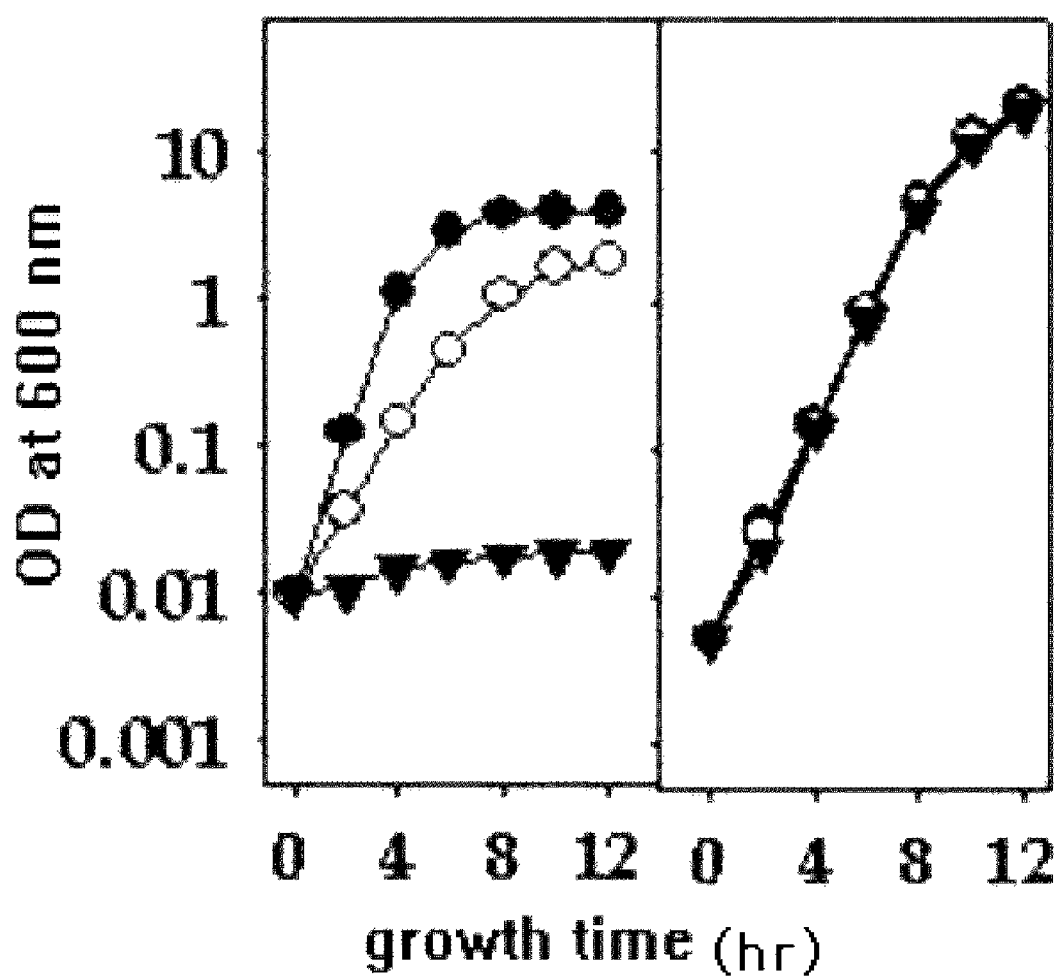
FIG. 6a is a graph showing the growth profiles of cells according to culture time. MG1655/pPHB-n (left panel) and MG1655/pTZ18U-PHB (right panel) cells were incubated in the supernatants collected from the MG1655/pTZ18U-PHB cultures grown in LB/glucose 7%/amp broth for 4 (●), 6 (○), and 8 hr (▼), respectively, and ODs were measured at the times indicated.
Figure 6B:
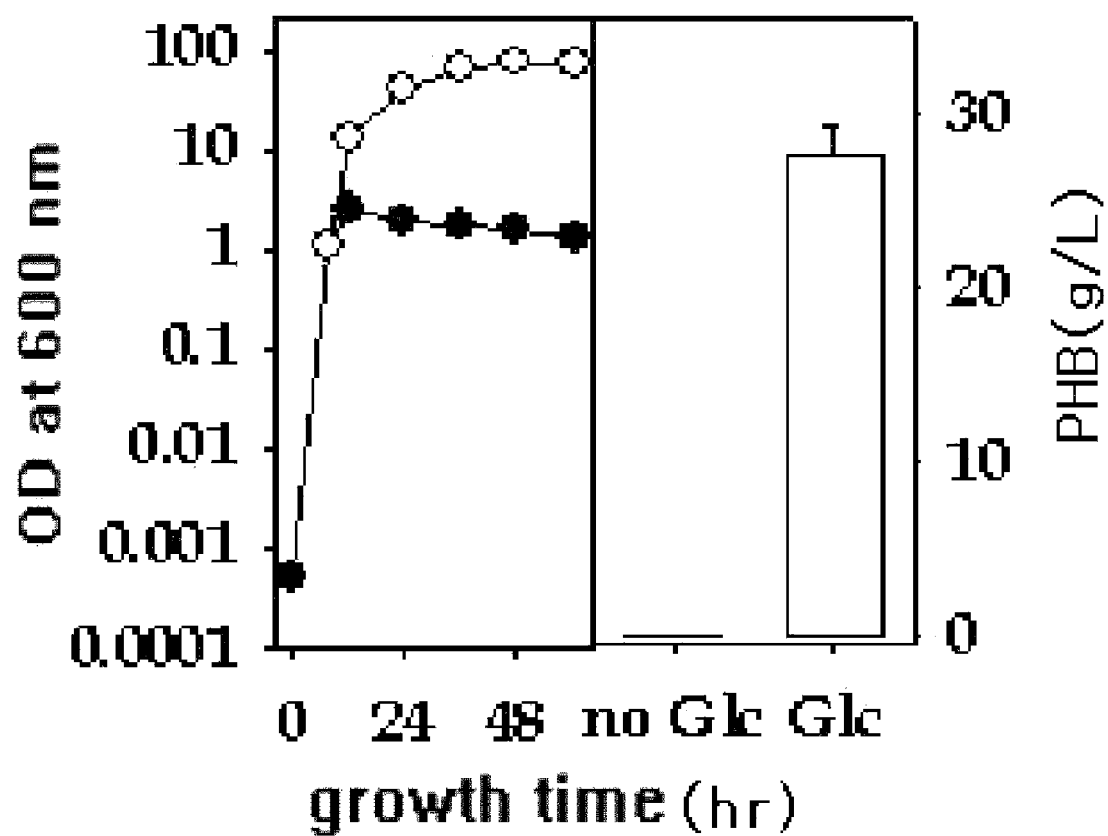
FIG. 6b is a graph showing the non-growth associated PHB production. MG1655/pTZ18U-PHB cells were grown in LB/amp broth for 8 hr and glucose 7% was added to the culture. OD (left panel) of cells cultured grown in LB/amp broth without glucose supplements (●) and with glucose (○) and final PHB concentrations (right panel) were measured.
Figure 6C:
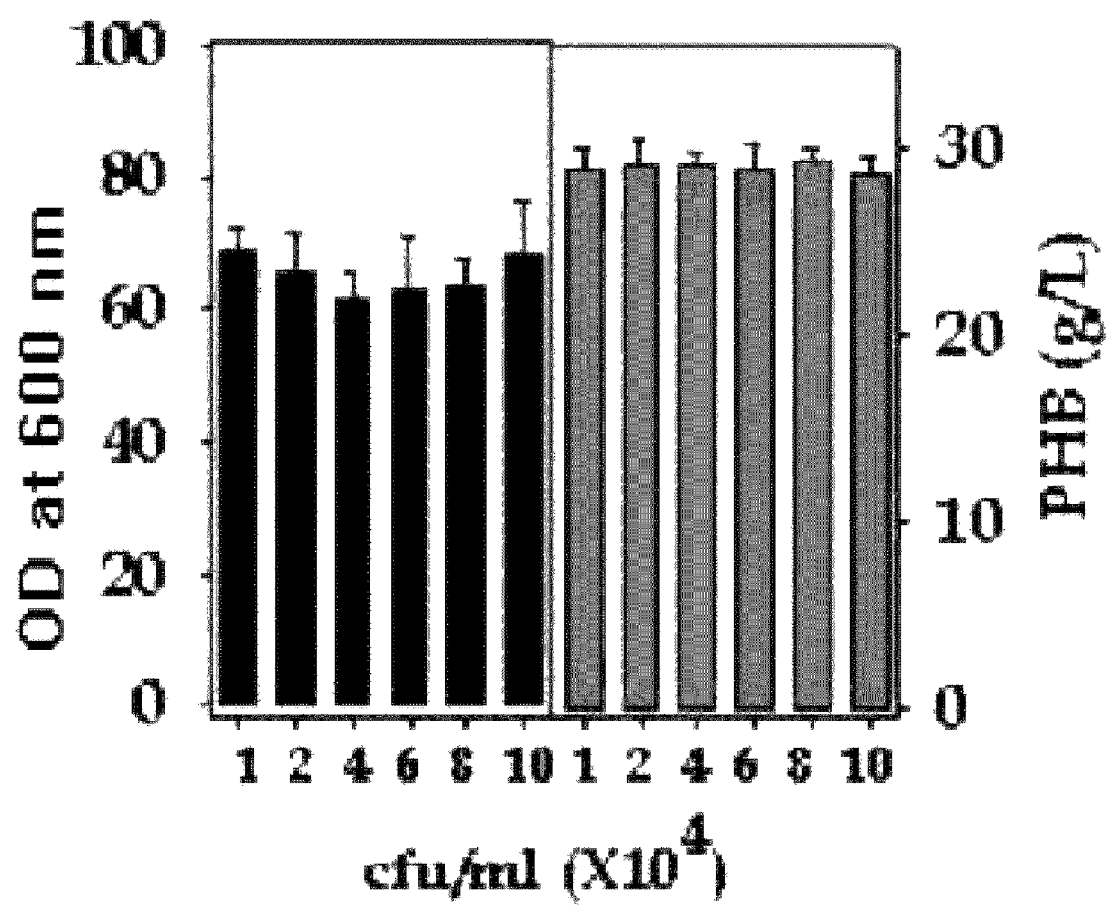

FIG. 6c is a graph showing the comparison of $OD_{600}$ (left panel) and PHB concentration (right panel). Different initial inoculum size ($10^4$~$10^5$ cells/ml) from MG1655/pTZ18U-PHB grown in LB/glucose 7%/amp broth for 8 hr was subcultured in the same fresh medium. OD and PHB concentrations were measured after 48 hr of cultivation.

Figure 6D:
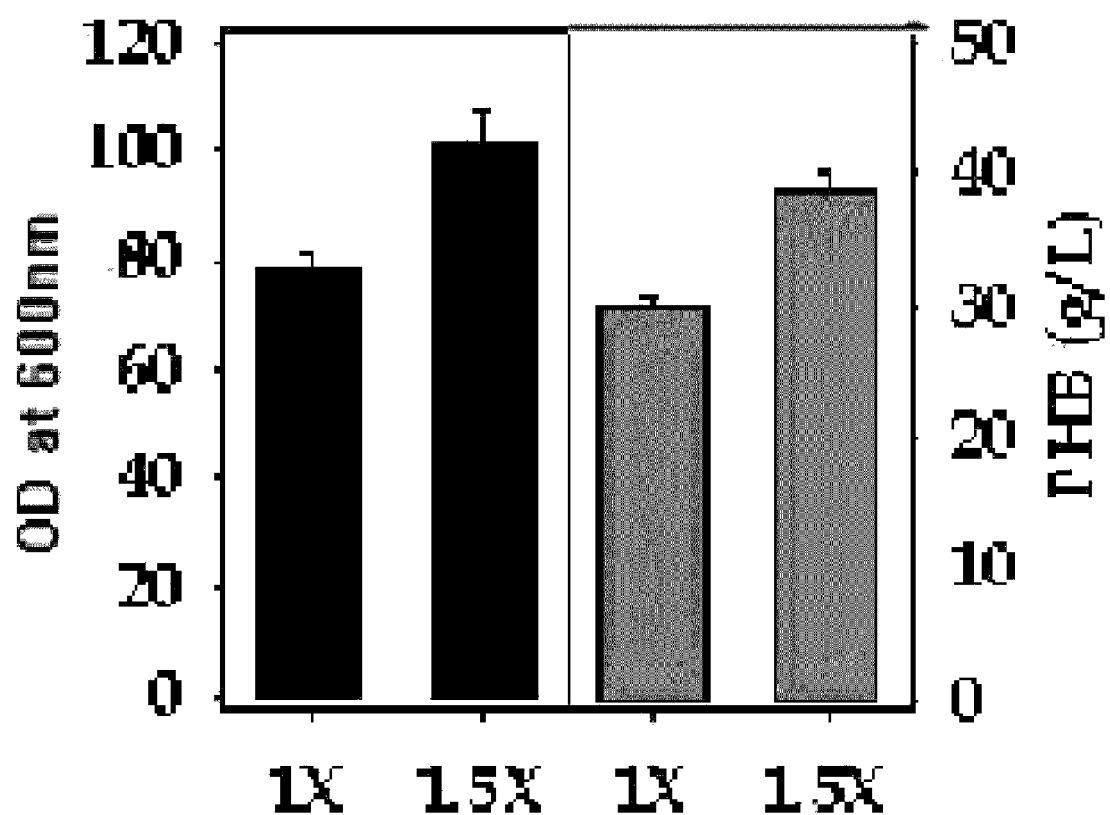

FIG. 6d is a graph showing the comparison of $OD_{600}$ (left panel) and PHB concentration (right panel). All the cells grown in the LB/glucose 7%/amp broth for 8 hr and its 1.5 times cell number were transferred in the supernatant of the culture grown in LB/glucose 7%/amp broth for 8 hr. OD and PHB concentrations were measured after 48 hr of cultivation.

Figure 7A:
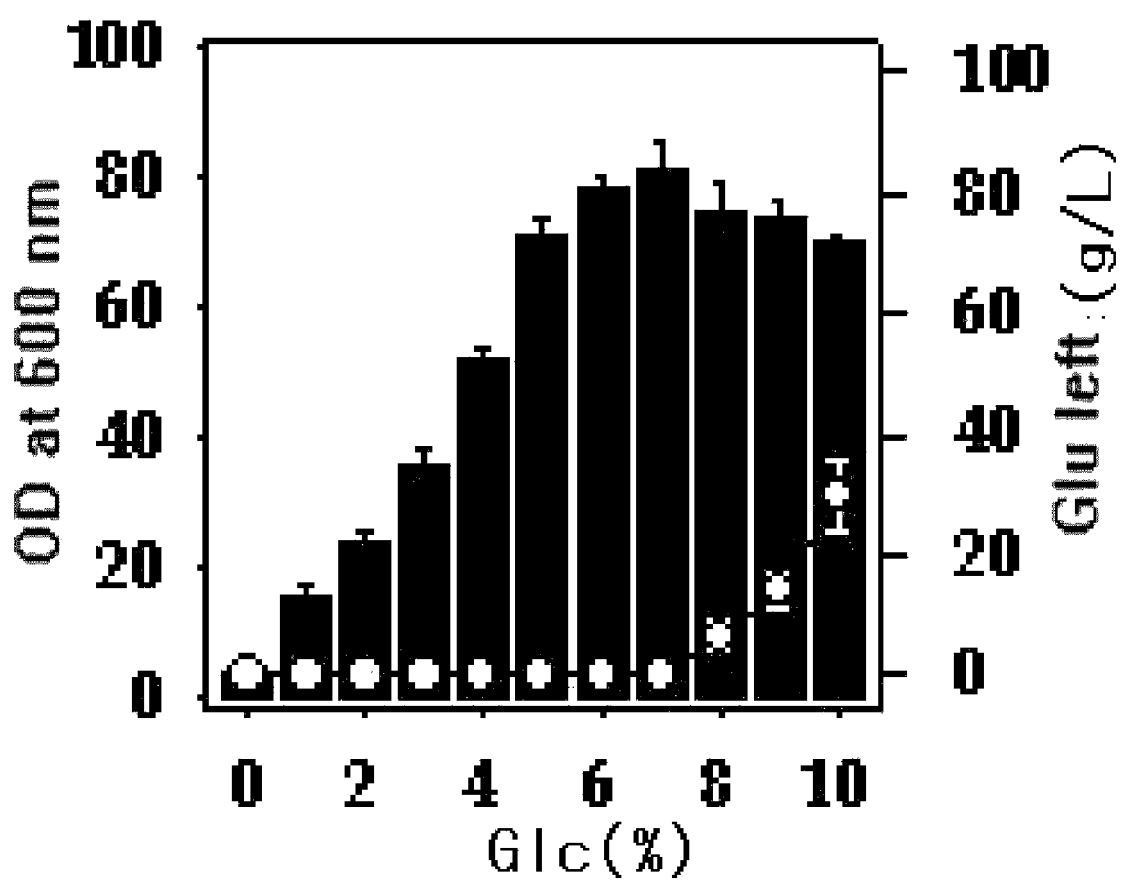

FIG. 7a is a graph showing the final OD (bar) and glucose left (○) according to glucose concentrations. MG1655/pTZ18U-PHB cells were inoculated in LB/glucose 0~10%/amp liquid media with a low inoculum size ($10^4$ cells/ml). OD and glucose concentrations were measured after 48 hr of cultivation.

Figure 7B:
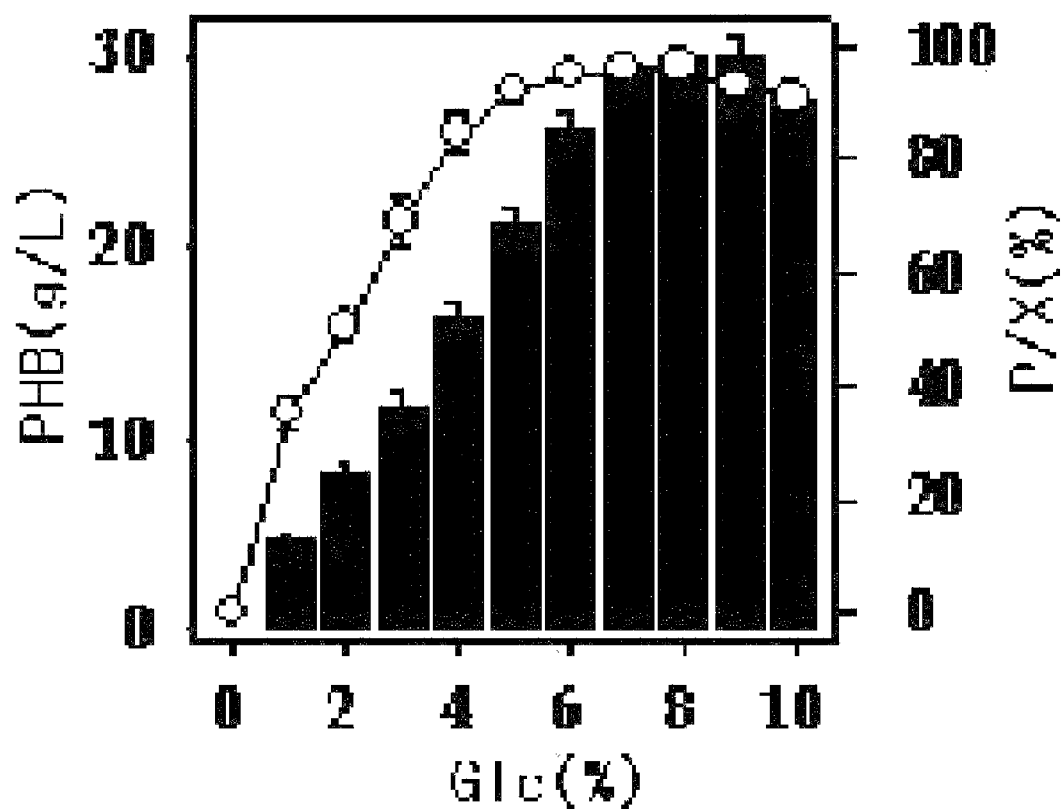

FIG. 7b is a graph showing the final PHB concentration (bar) and content (P/X, %, ○) according to glucose concentrations. MG1655/pTZ18U-PHB cells were inoculated in LB/glucose 0~10%/amp liquid media with a low inoculum size ($10^4$ cells/ml). Final PHB concentration and content were measured after 48 hr of cultivation.

FIG. 7c is a graph showing the OD (●) and glucose remaining (○) during growth of LB/glucose 7%/amp. MG1655/pTZ18U-PHB cells were inoculated in LB/glucose 7%/amp liquid medium with a low inoculum size ($10^4$ cells/ml). According to culture time, ODs and glucose contents were measured.

Figure 7D:
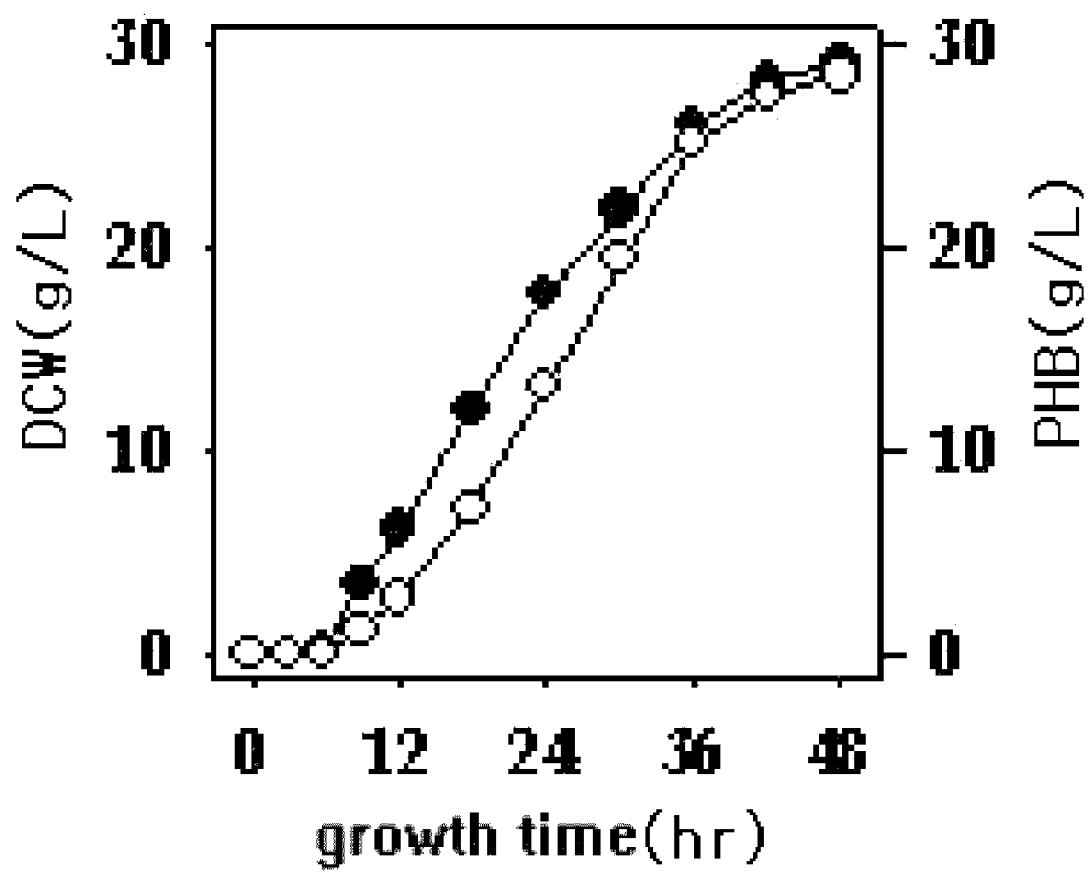

FIG. 7d is a graph showing the dry cell weight (DCW, ●) and PHB concentrations (○) during growth in LB/glucose 7%. MG1655/pTZ18U-PHB cells were inoculated in LB/glucose 7%/amp liquid medium with a low inoculum size ($10^4$ cells/ml). According to culture time, DCW and PHB concentrations were measured.

Figure 7E:
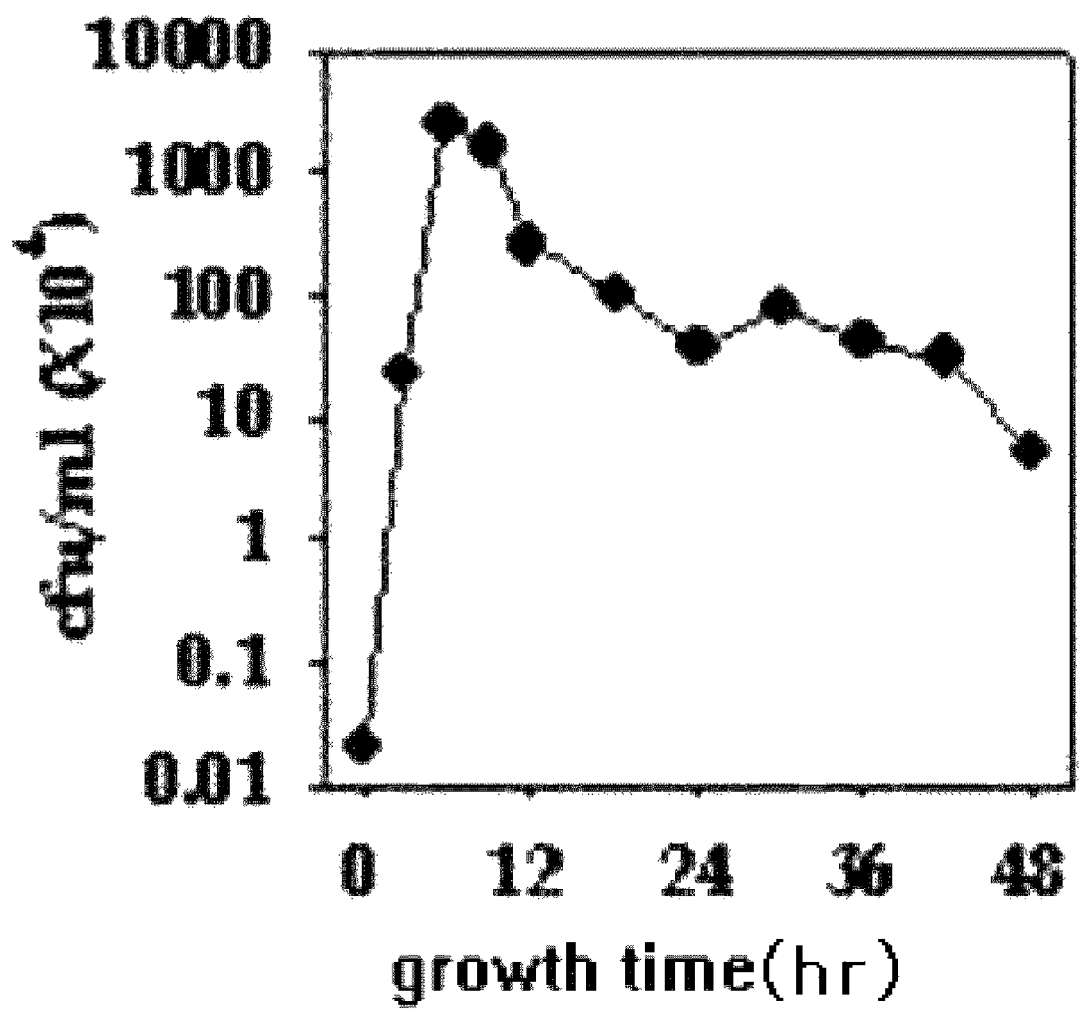

FIG. 7e is a graph showing the viable cell number (cfu/ml) during growth of LB/glucose 7%/amp. MG1655/pTZ18U-PHB cells were inoculated in LB/glucose 7%/amp liquid medium with a low inoculum size ($10^4$ cells/ml). According to culture time, viable cell number was measured.

Figure 7F:
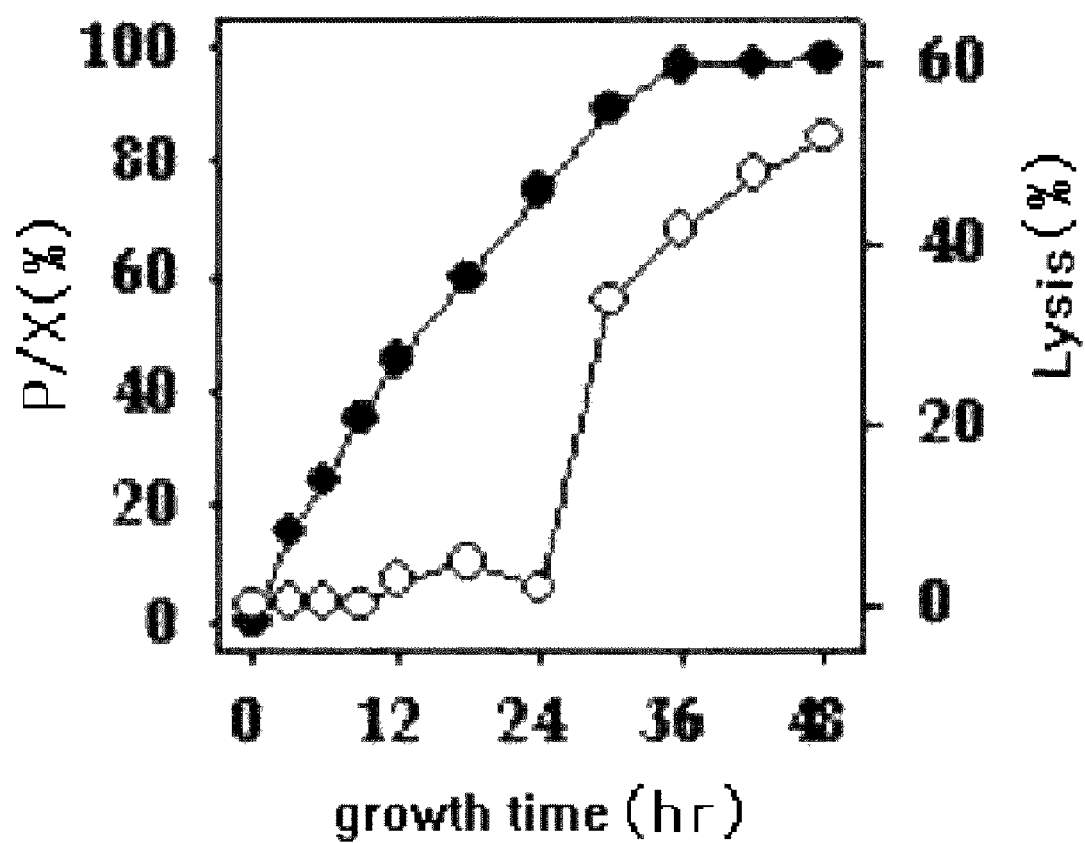

FIG. 7f is a graph showing the PHB content (●) and autolysis (%, ○) during growth of LB/glucose 7%/amp. MG1655/pTZ18U-PHB cells were inoculated in LB/glucose 7%/amp liquid medium with a low inoculum size ($10^4$ cells/ml). According to culture time, PHB content and autolysis were measured.

Figure 8:
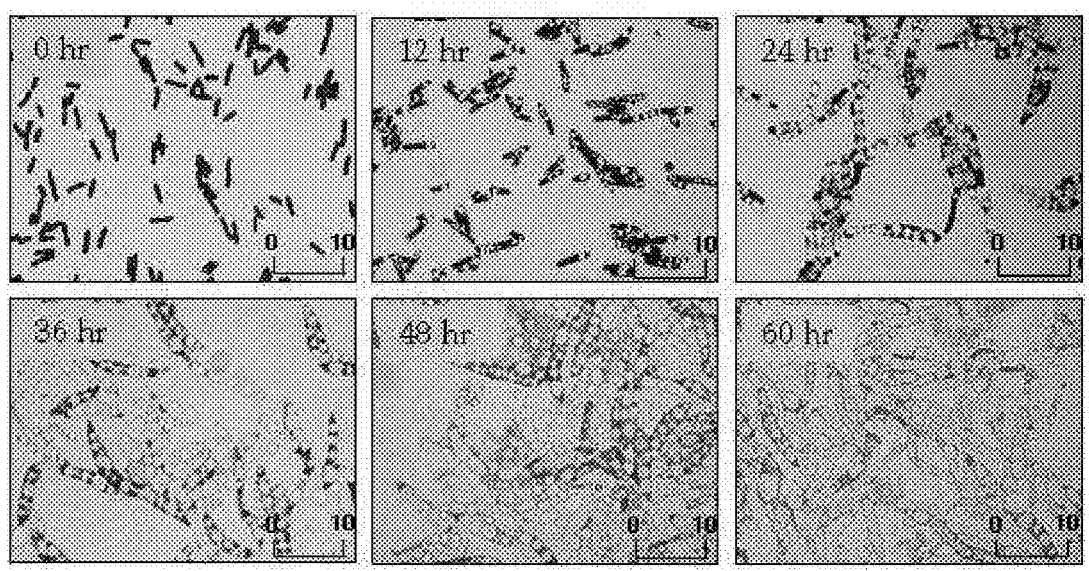

FIG. 8 is a set of microphotographs (×1,000) showing the change of cell morphology according to culture time. MG1655/pTZ18U-PHB cells were inoculated in LB/glucose 7%/amp liquid medium with a low inoculum size ($10^4$ cells/ml).

Figure 9A:
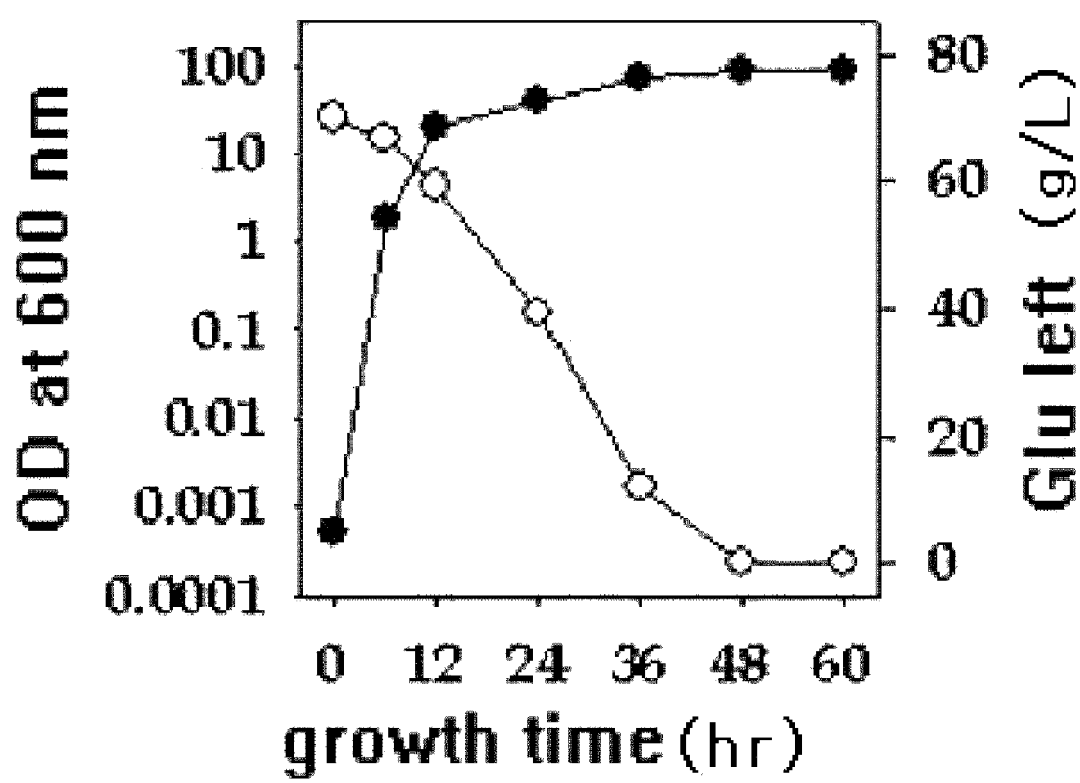

FIG. 9a is a graph showing the OD (●) and glucose remaining (○) during growth in LB/glucose 7%. MG1655/pTZ18U-PHB cells were inoculated in 2×LB/glucose 7%/amp liquid medium with a low inoculum size ($10^4$ cells/ml). According to culture time, ODs and glucose concentrations were measured.

Figure 9B:
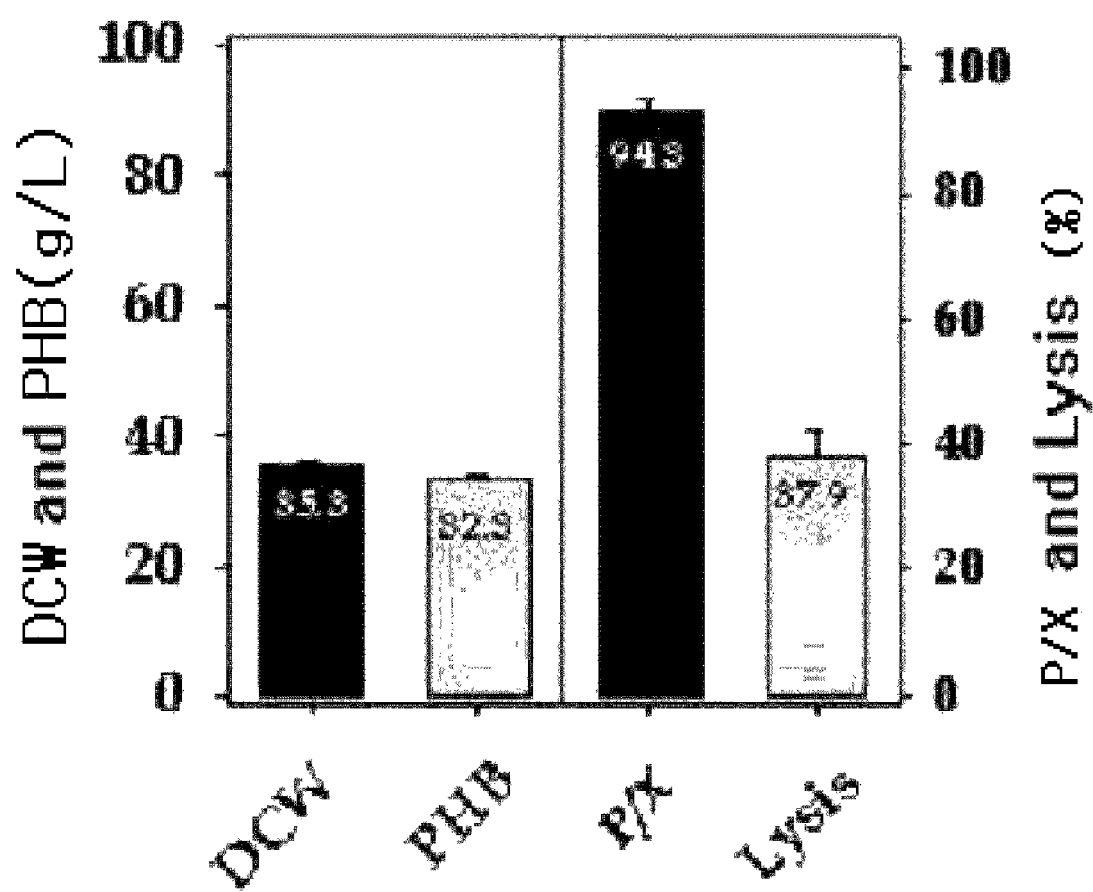

FIG. 9b is a graph showing the final DCW, PHB, PHB content (P/X, %) and autolysis (%) after 60 hr of cultivation in 2×LB/glucose 7%.

Figure 9C:
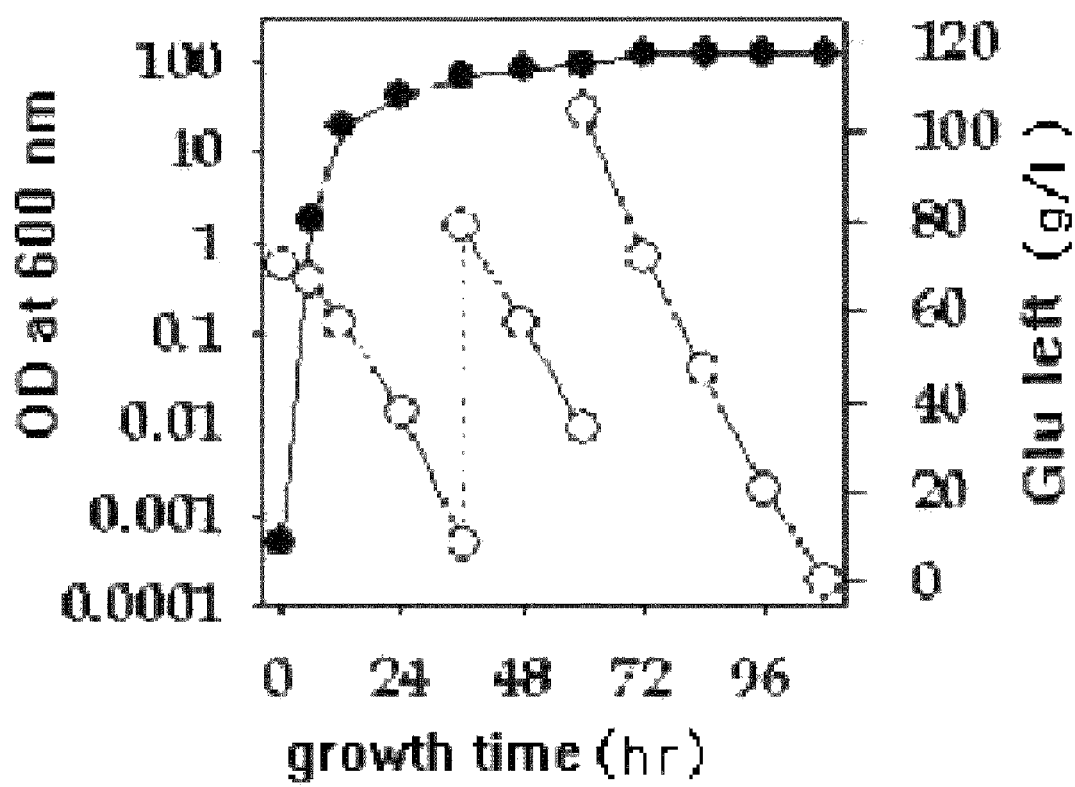

FIG. 9c is a graph showing the OD (●) and glucose remaining (○) during growth in LB/glucose 21%. MG1655/pTZ18U-PHB cells were inoculated in 2×LB/glucose 21% total/amp liquid medium with a low inoculum size ($10^4$ cells/ml). Glucose (7%) was added intermittently at 0, 36 and 60 hr of cultivation.

Figure 9D:
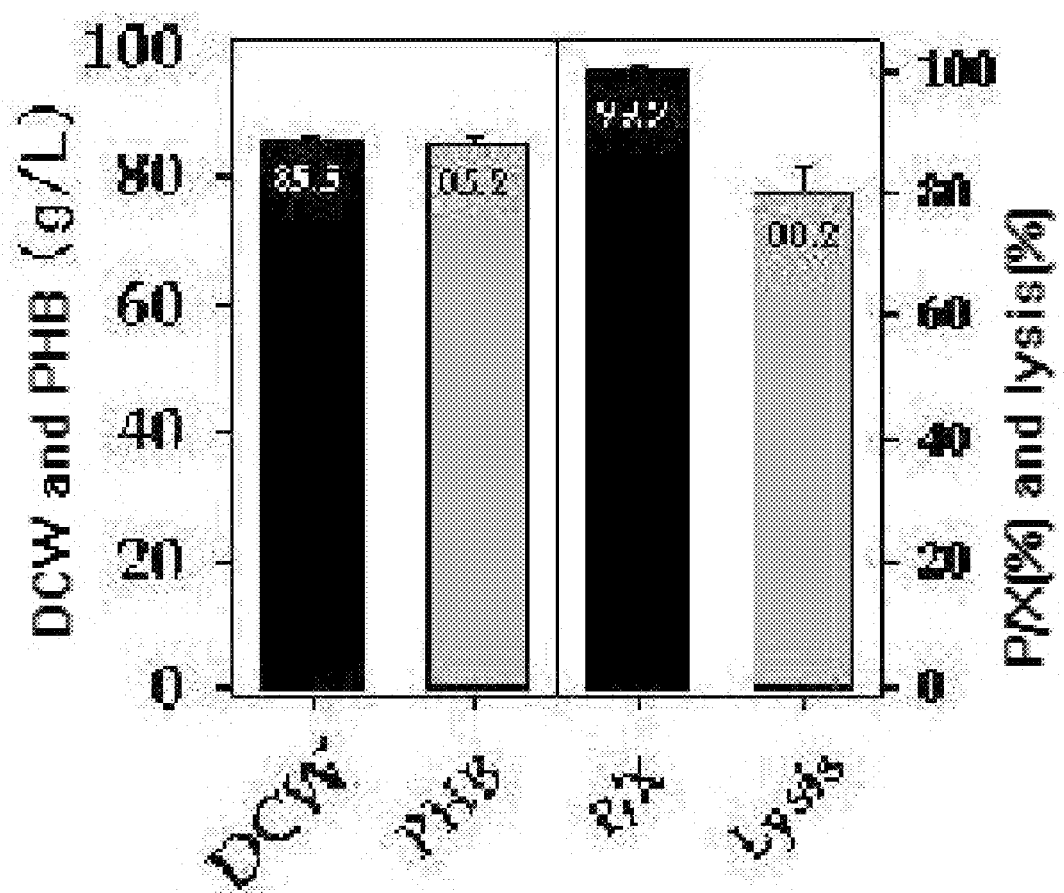

FIG. 9d is a graph showing the final DCW, PHB, PHB content (P/X, %) and autolysis (%) after 60 hr of cultivation in 2×LB/glucose 21%. MG1655/pTZ18U-PHB cells were inoculated in 2×LB/glucose 21% total/amp liquid medium with a low inoculum size ($10^4$ cells/ml). Glucose (7%) was added intermittently at 0, 36 and 60 hr of cultivation.

Figure 10A:
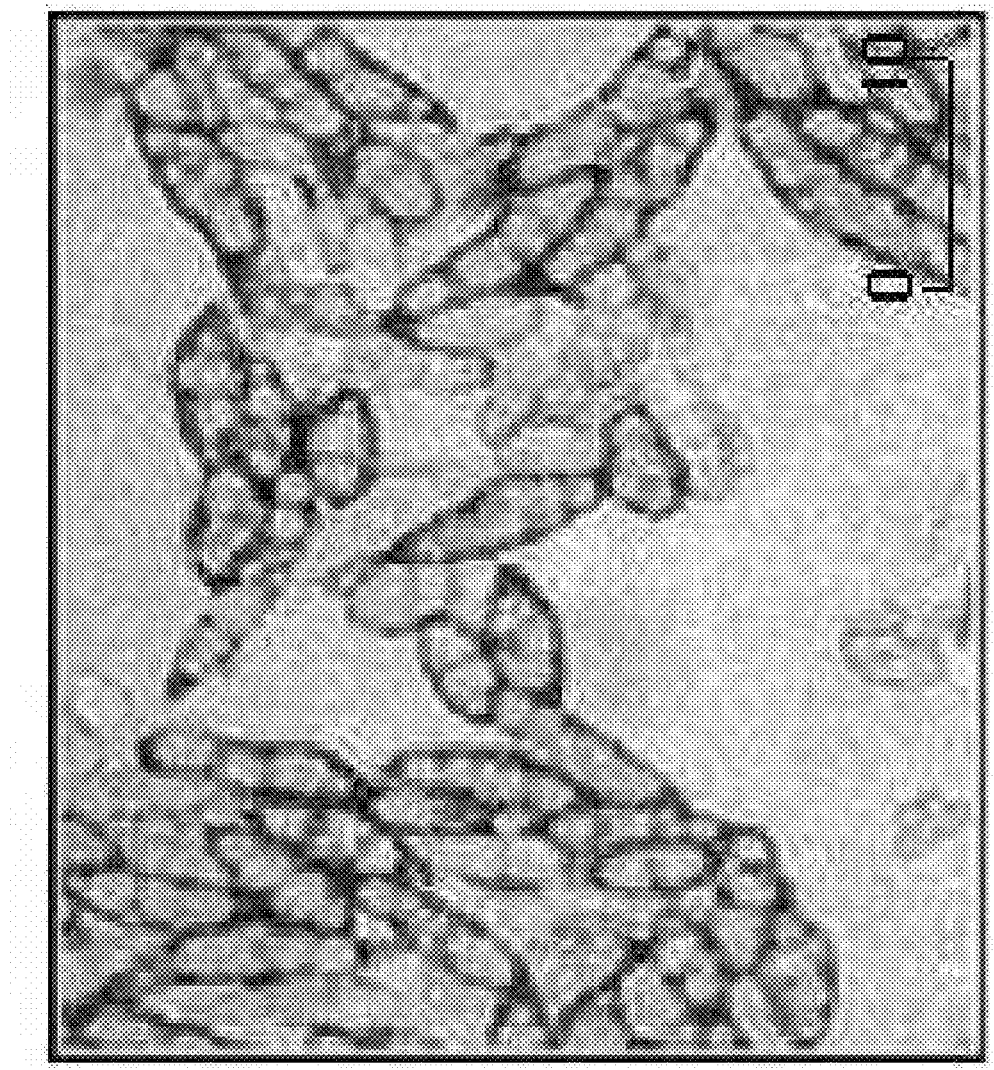

FIG. 10a is a microphotograph (×1,000) showing the MG1655/pTZ18U-PHB cells inoculated in 2×LB/glucose 7%/amp liquid medium with a low inoculum size ($10^4$ cells/ml).

Figure 10B:
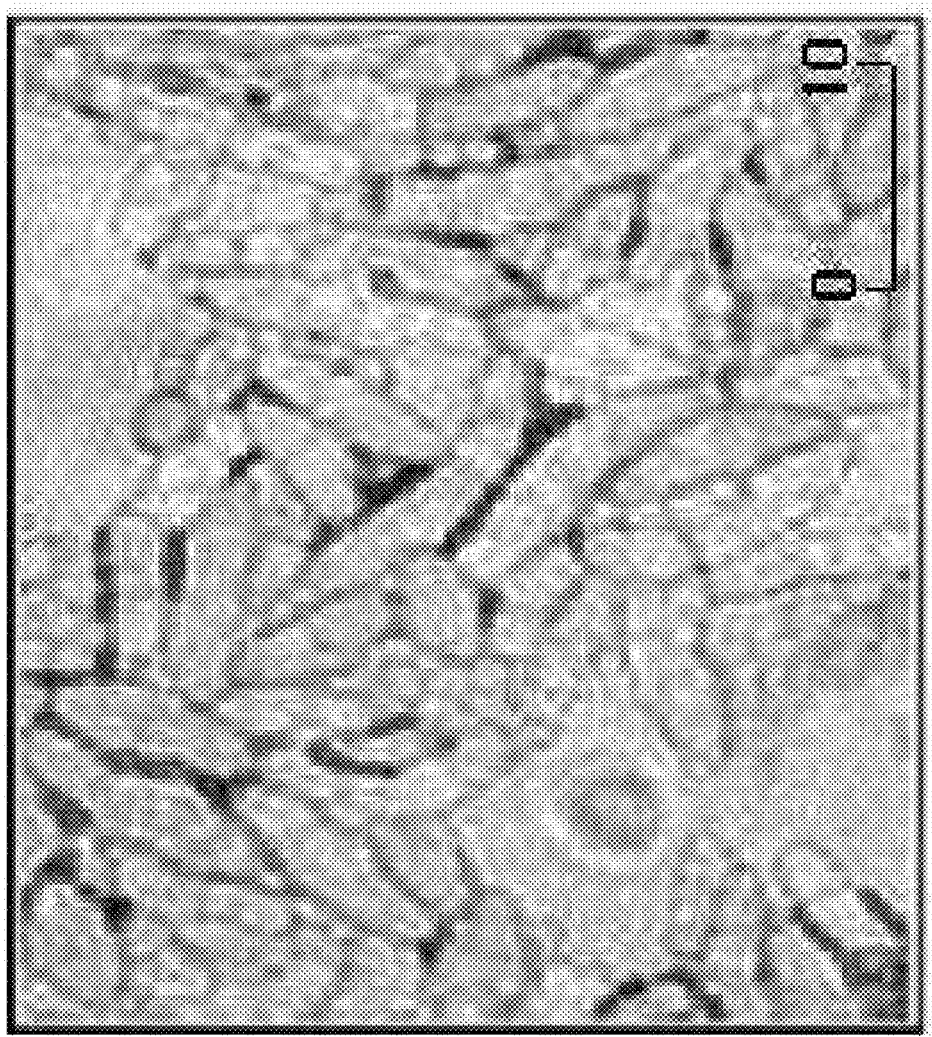

FIG. 10b is a microphotograph (×1,000) showing the MG1655/pTZ18U-PHB cells inoculated in 2×LB/glucose 21%/amp liquid medium with a low inoculum size ($10^4$ cells/ml).

Figure 10C:
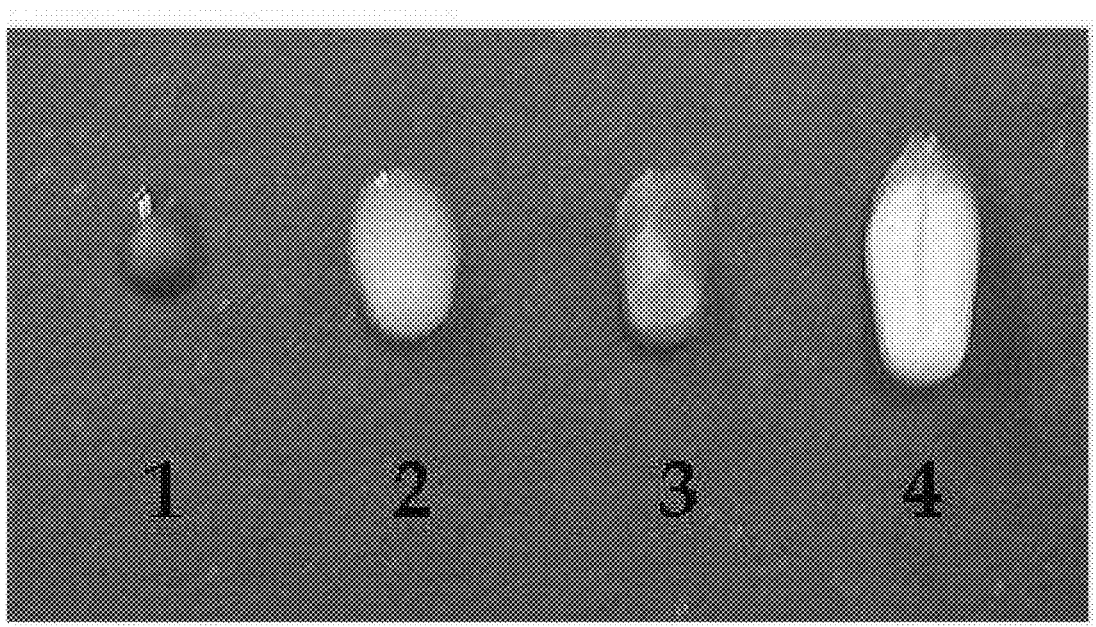

FIG. 10c is a photograph showing the final dried cells of MG1655/pTZ18U-PHB inoculated in 1× or 2×LB/glucose/amp liquid medium with a low inoculum size ($10^4$ cells/<).

1: 1×LB/amp medium (without glucose),
2: 1×LB/glucose 7%/amp medium,
3: 2×LB/glucose 7%/amp medium,
4: 2×LB/glucose 21% total/amp medium.

Figure 11:
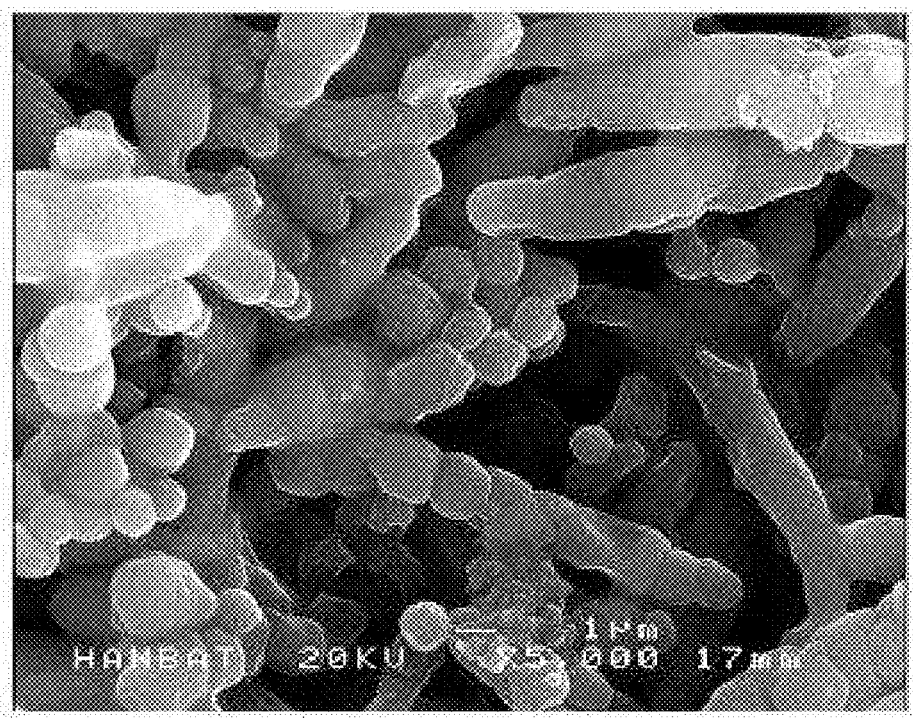
Figure 11:
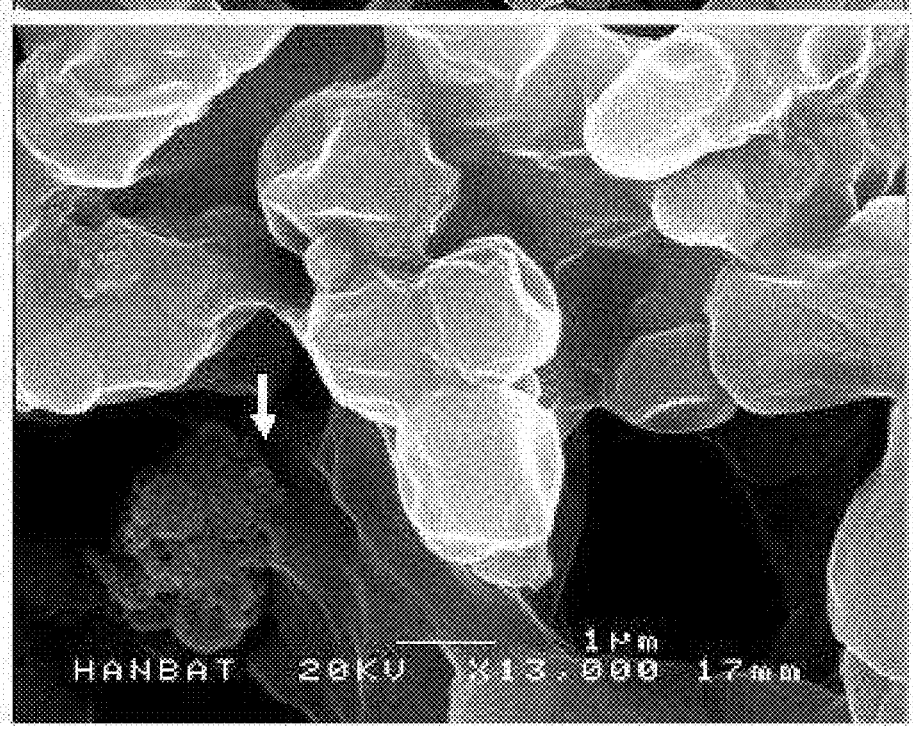

FIG. 11 is a set of scanning electron microphotographs showing the MG1655/pTZ18U-PHB cells (a) inoculated in 2×LB/glucose 21%/amp liquid medium with a low inoculum size ($10^4$ cells/ml) and PHB autolysis (b).

Figure 12A:
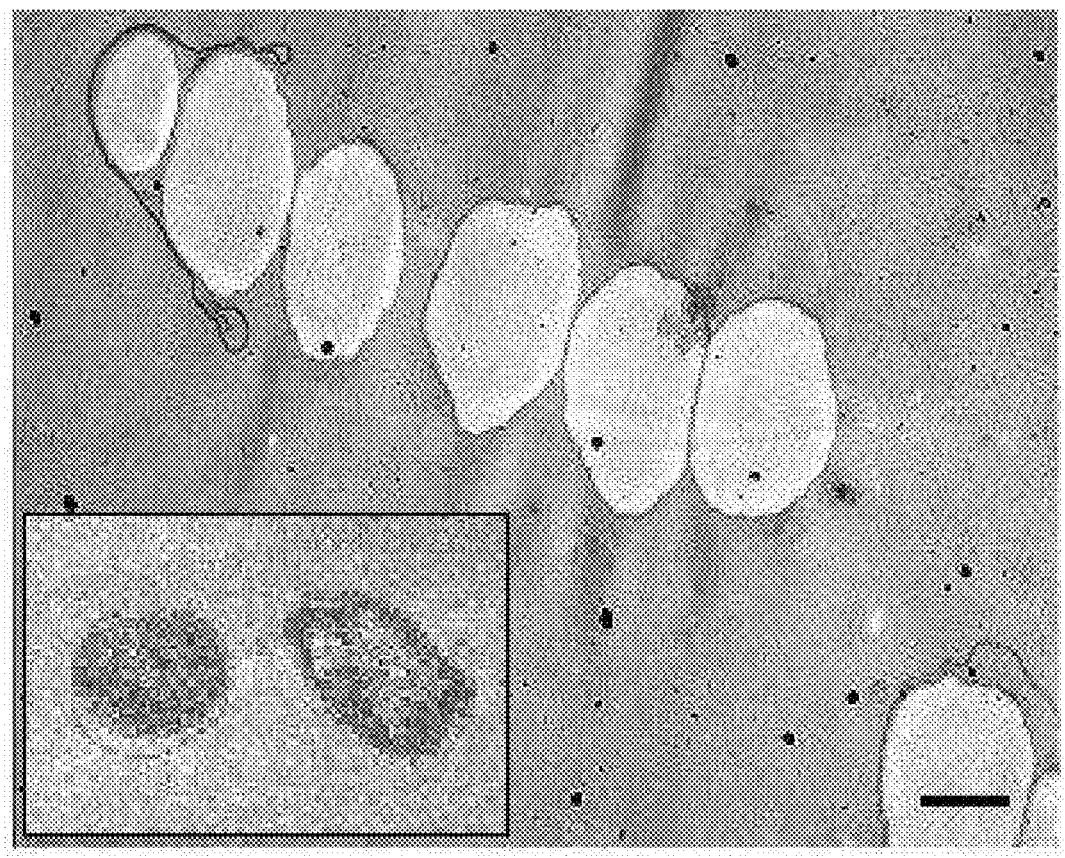

FIG. 12a is a transmission electron microphotograph showing the MG1655/pTZ18U-PHB cells inoculated in 2×LB/glucose 21%/amp liquid medium with a low inoculum size ($10^4$ cells/ml) and MG1655/pPHB-n cells (insertion sheet) inoculated in 2×LB/glucose 21%/amp liquid medium with a low inoculum size (Scale bar indicates 1 μm).

Figure 12B:
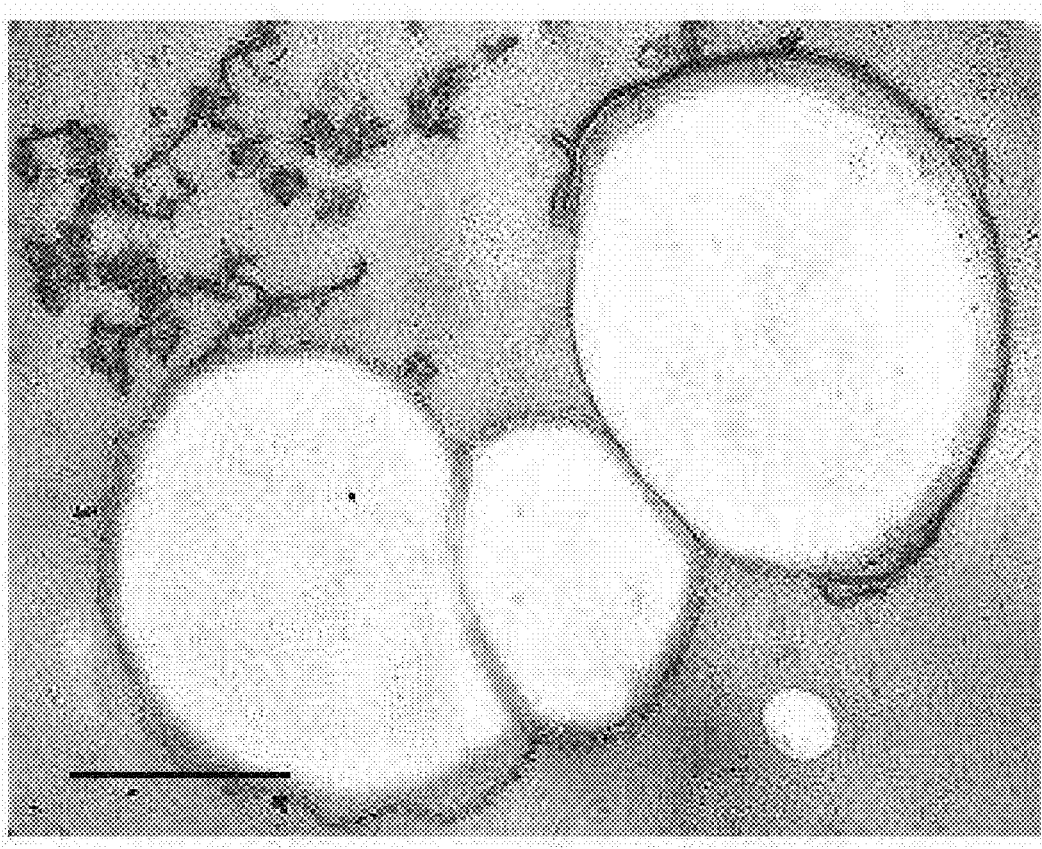

FIG. 12b is a transmission electron microphotograph showing that MG1655/pTZ18U-PHB cell membranes are cut off and internal PHB granules are lysed spontaneously outside the cell.

EXAMPLES

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1

Preparation of a Transgenic *E. coli* Strain Harboring PHB Gene and Stock Seeds

<1-1> Preparation of a Plasmid and a Transgenic *E. coli* Strain

Plasmid 'pTZ18U-PHB' harboring phbCAB gene was distributed from professor Jung Kuk Lee, Sogang University, Seoul, Korea, who had kept the plasmid previously provided from Dr. Alexander Steinbuchel, Munster University, Germany. phbCAB gene is composed of phbC gene, phbA gene and phbB gene and a sequence of each gene is represented by SEQ ID NO: 1, SEQ ID NO: 2 and SEQ ID NO: 3, respectively.

Wild type strain MG1655 (CGSC, Coli Genetic Stock Center, Yale University, CT, USA), an inducible strain of *E. coli* K-12, was used as a host strain. The strain was transformed by pTZ18U-PHB plasmid according to a conventional method using $CaCl_2$ (Sambrook, J. and Russell, D. W., Laboratory Press. Cold Spring Harbor, N.Y. 2001). The transformant was streaked onto LB/amp agar plate and the growing strains on the plate were selected as final transformants.

<1-2> Preparation of Stock Seeds by Culturing the Transformed *E. coli*

Colonies formed in the recombinant *E. coli* prepared in the above example <1-1> were cultured on LB plate (Bacto tryptone 10 g/l; Bacto-yeast extract 5 g/l; NaCl 10 g/l) for 12 hours. Antibiotics, tetracycline and ampicilin (amp), were added to the medium by 20 μg/ml and 100 μg/ml each. A colony grown in the medium was taken to be inoculated on LB/amp medium, followed by further culture until $OD_{600}$ reached 0.2. Cells were harvested and suspended in LB/20% glycerol medium to reach $5\times10^8$ cfu/ml. Each 0.1 ml of the suspension was poured into microcentrifuge tubes and stored at −80° C. They were used as stock seeds.

After one microcentrifuge tube was thawed at room temperature, stock seeds (20 μl) were inoculated onto LB/amp agar plate and cultured in a shaking incubator at 37° C., 200 rpm. The seed cultures were diluted in 250 ml conical flask containing 10 ml of LB/glucose/amp, then they were further shaking-cultured again at 37° C., 200 rpm.

Example 2

Effects of Initial Inoculum Size on PHB Production

<2-1> Colony Formation According to Initial Inoculum Size

Figure 1:
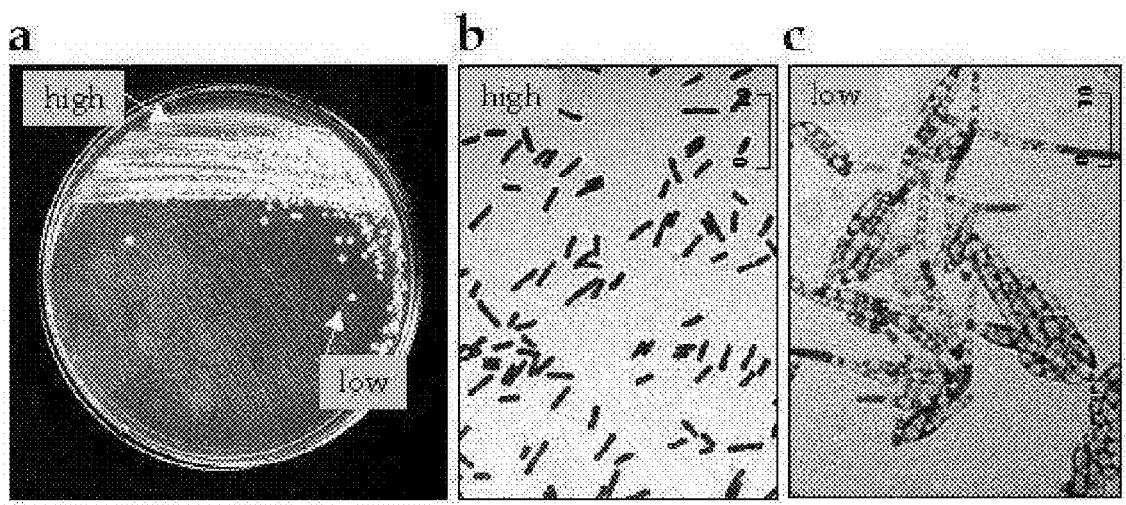
FIG. 1 is a set of photographs showing the effect of the initial inoculum size. All recombinant MG1655/pTZ18U-PHB cells were cultured in LB/glucose 5%/amp/1.5% agar solid medium. (a) Phenotype of host strain according to the initial inoculum size. (b) Microphotograph (×1,000) of host strain grown in high region. (c) Microphotograph (×1,000) of host strain grown in low region.

When recombinant *E. coli* MG1655, a host strain, containing pTZ18U-PHB plasmid prepared in the above example <1-1> was streaked onto LB/glucose 7%/amp agar plate, two types of colonies were visualized. The one in the "high" region whose inoculum size was high and cells were very close together, showed a representative brown color of *E. coli*. The other in "low" region, whose inoculum size was low and cells were apart from each other, showed a white-opaque color (FIG. 1a). While no intracellular PHB was found in the cells of "high" region, a large amount of PHB existed in the cells of "low" region (FIG. 1b and FIG. 1c).

<2-2> PHB Production According to Initial Inoculum Size

Figure 2:
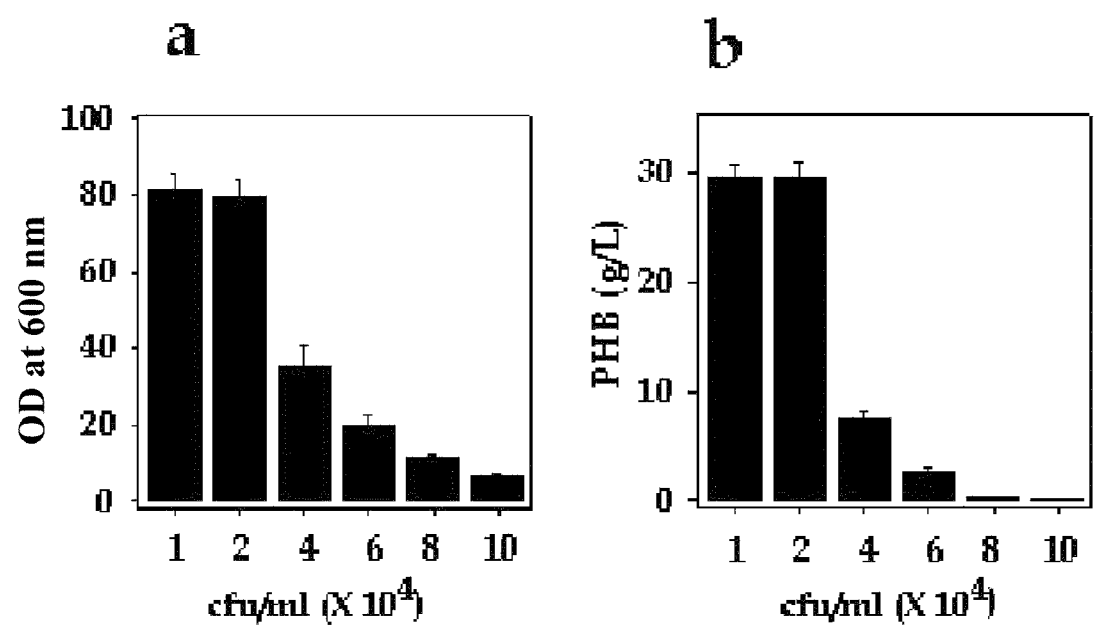
FIG. 2 is a set of graphs showing the comparison of $OD_{600}$ (a) and PHB concentration (b) according to the initial inoculum size. Cells were incubated in either relative high—(5 mL medium volume) or low (10 mL medium volume)—aerated culture flask.

In order to confirm if PHB production observed above was affected by initial inoculum size, the present inventors investigated PHB accumulation under various inoculum sizes ranging $10^4$~$10^5$ cells/ml (FIG. 2). Intracellular PHB production was measured by gas chromatography (Varian 3300, USA).

Particularly, one microcentrifuge tube (stock seed) under the storage at −80° C. was thawed at room temperature. Then, 20 μl was transferred into a 125 ml conical flask containing 10 ml of LB/amp medium. Cells were cultured at 37° C., 200 rpm, which were inoculated into a 250 ml conical flask containing 10 ml of LB/glucose 7%/amp medium concentration by concentration. As a result, the lower the inoculum size was, the higher the OD at 600 nm and the final PHB production became. In particular, when inoculum size was $10^4$ cells/ml, the highest PHB production was observed. From the results, it was confirmed that initial inoculum size acted as an important factor for intracellular PHB production.

Example 3

Cell Number and Preparation of Capable Cells

Figure 3:
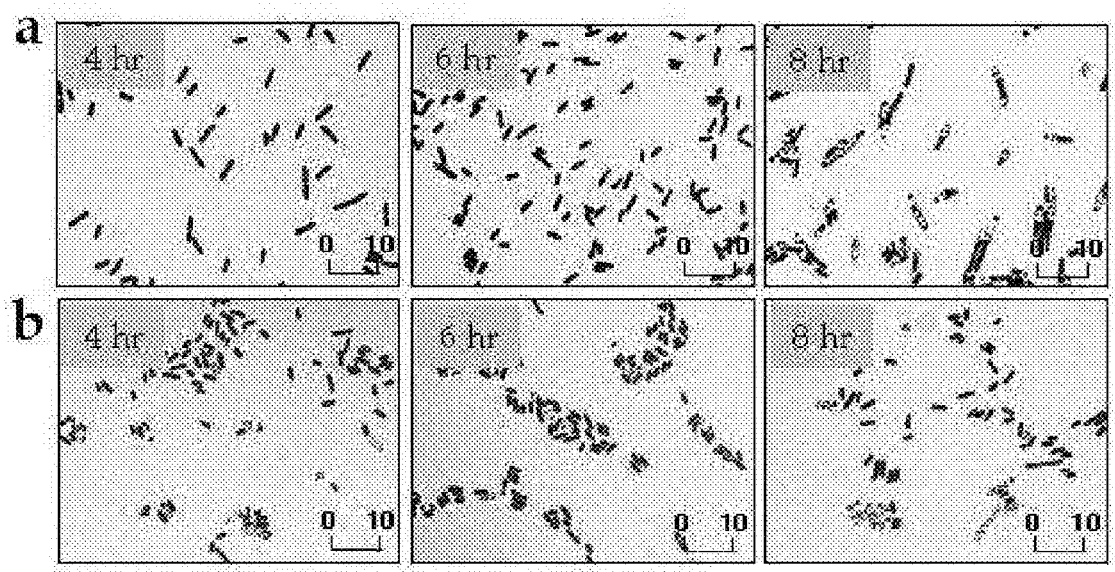
FIG. 3 is a set of microphotographs showing the light microscopic views of cells grown from low inoculum ($10^4$ cells/ml) (a) and high inoculum ($10^5$ cells/ml) (b) size. Magnification is ×1,000 and bars indicate 10 μM.

In order to verify that low inoculum size was advantageous to PHB production, the present inventors investigated changes in cell morphology and patterns of PHB accumulation, during the early stage of cell growth, by light microscopy (FIG. 3). As a result, PHB was visualized after 8 hour of cultivation with a low inoculum size ($10^4$ cells/ml) On the contrary, although PHB accumulation was shown at an early culture time (after 4 hour of cultivation) with a high inoculum size ($10^5$ cells/ml), cells producing PHB or not were mixed together at that time.

Figure 4A:
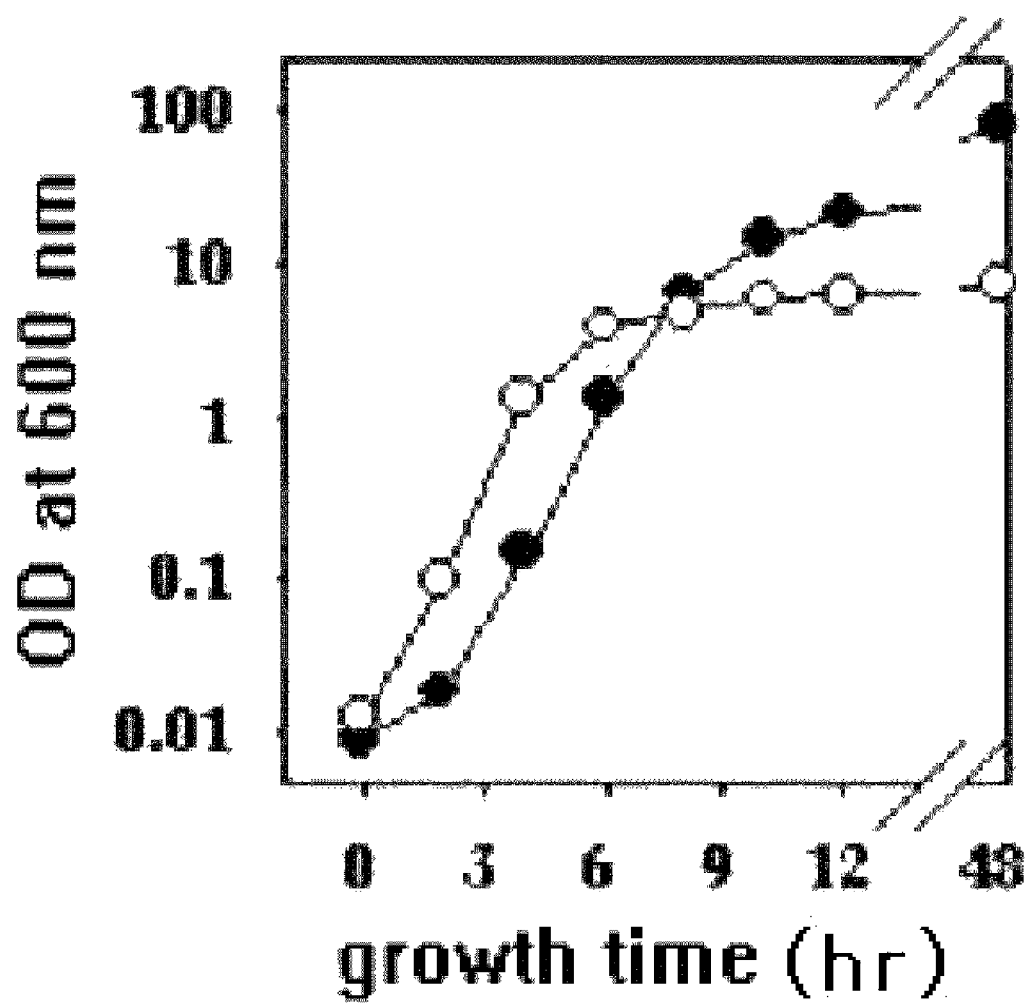
FIG. 4a is a graph showing the growth profiles ($OD_{600}$) of cells inoculated with low ($10^4$ cells/ml, ●), and high inoculum size ($10^5$ cells/ml, ○). Cells were cultured in LB/glucose 7%/amp medium.

This phenomenon was reflected in optical cell density (FIG. 4a). The initial OD (reflecting cell growth) with a high inoculum size was higher (0~6 hour of cultivation) than that with a low inoculum size, but OD of low inoculum size became higher after 8 hour of cultivation. This reversion resulted from effective PHB accumulation in the low inoculum size.

Figure 4B:
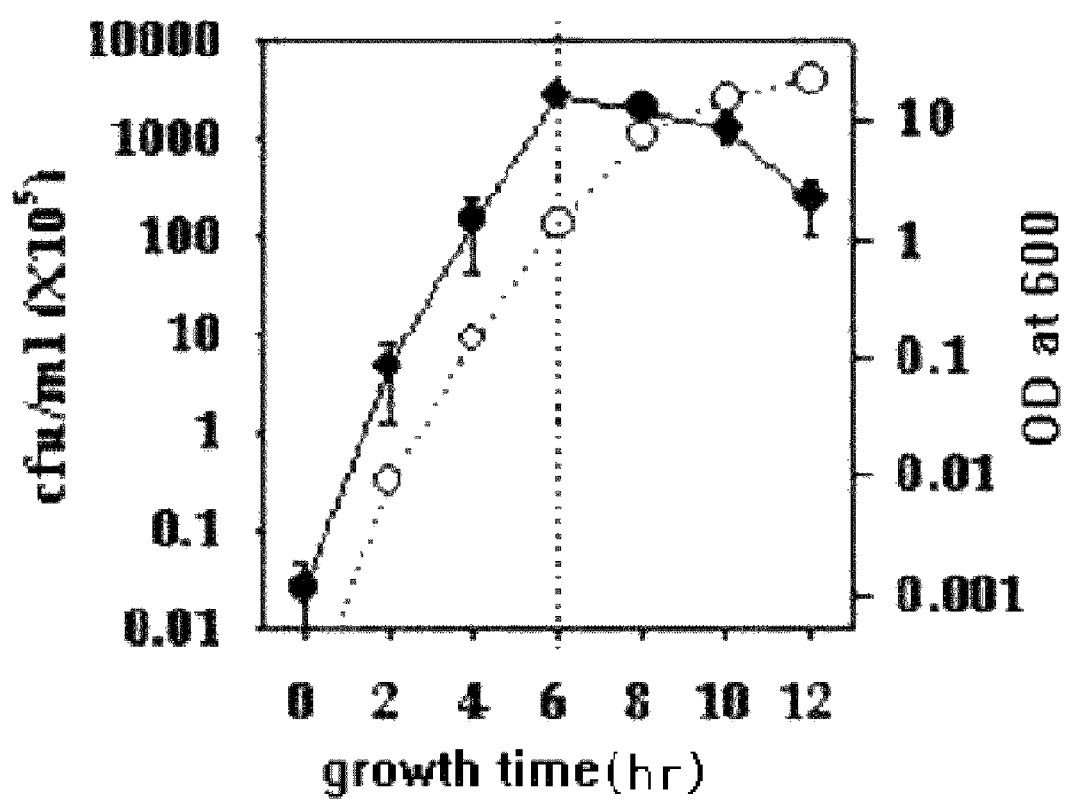
FIG. 4b is a graph showing the changes of viable cell number (cfu, ●) and growth profiles ($OD_{600}$, ○) according to culture time. Cells were inoculated onto LB/glucose 7%/amp plate with low inoculum size ($10^4$ cells/ml).

In order to re-confirm the above result, the present inventors measured the number of viable cells (cfu/ml). Particularly, samples were taken several times during the culture, which were then diluted with PBS (phosphate buffered saline). The samples were distributed on LB/glucose 5%/amp agar plate and further cultured at 37° C. for 24 hours. The grown up cells on the medium were counted to determine the number of viable cells. As a result, cells reached the maximum number at 6 hour of cultivation in a low inoculum size, and from then on, cells did not increased (FIG. 4b). Nevertheless, OD was continued to increase, reaching 80 after 48 hours. That was resulted from intracellular PHB accumulation.

Figure 4C:
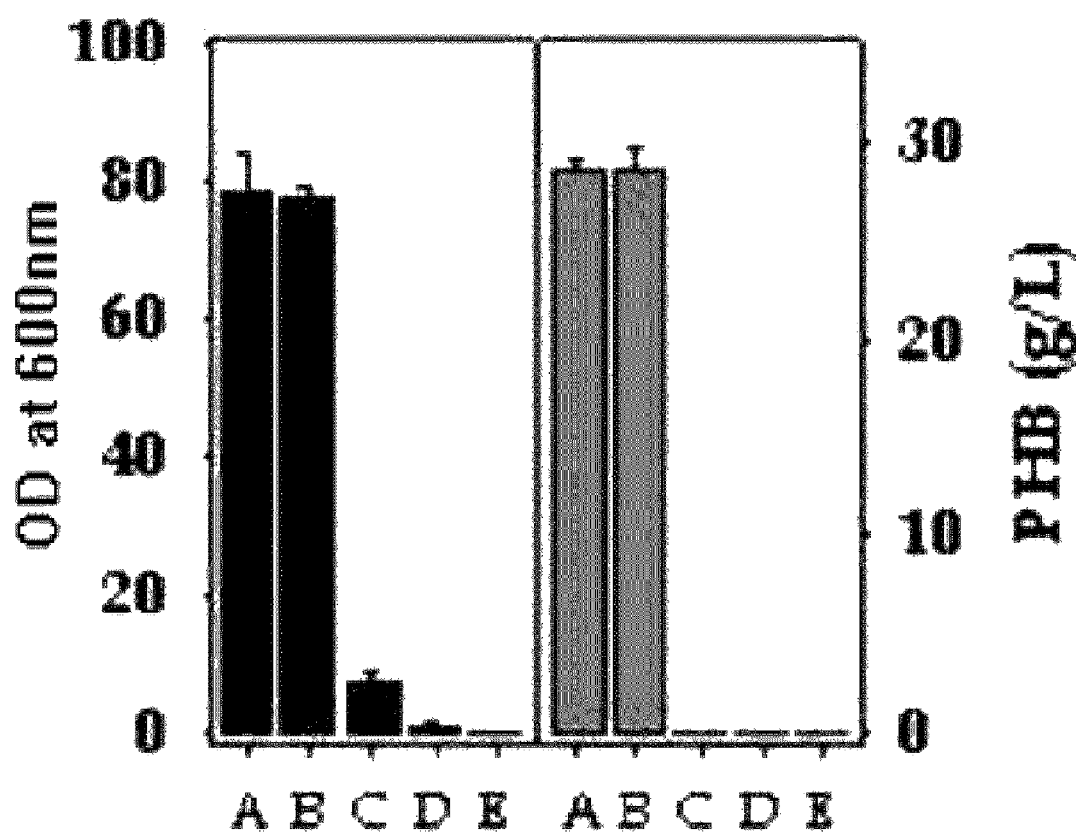
FIG. 4c is a graph showing the comparison of $OD_{600}$ (left) and PHB concentration (right) according to culture conditions, A: Cells grown for 8 hr after inoculating in LB/glucose 7%/amp liquid medium with a low inoculum size ($10^4$ cells/ml) were harvested and all the cells were transferred to the supernatant obtained from the culture grown for 8 hr after inoculating in LB/glucose 7%/amp liquid medium with a low inoculum size ($10^4$ cells/ml), B: Cells grown for 8 hr after inoculating in LB/glucose 7%/amp liquid medium with a low inoculum size ($10^4$ cells/ml) were harvested and all the cells were transferred to the supernatant obtained from the culture grown for 8 hr after inoculating in LB/glucose 7%/amp liquid medium with a high inoculum size ($10^5$ cells/ml), C: Cells grown for 8 hr after inoculating in LB/glucose 7%/amp liquid medium with a high inoculum size ($10^5$ cells/ml) were harvested and all the cells were transferred to the supernatant obtained from the culture grown for 8 hr after inoculating in LB/glucose 7%/amp liquid medium with a low inoculum size ($10^4$ cells/ml), D: Cells grown for 8 hr by high-inoculum culture were harvested and 1/10 of the cells were transferred to the supernatant obtained from the culture grown for 8 hr by low inoculum ($10^4$ cells/ml), E: Cells grown for 8 hr by high-inoculum culture were harvested and 1/100 of the cells were transferred to the supernatant obtained from the culture grown for 8 hr by low inoculum ($10^4$ cells/ml).

As explained hereinbefore, cells did not increase further after 8 hour of cultivation in a low inoculum size but OD and PHB concentration did increased. To understand the possible mechanism, we compared the following (FIG. 4c):

"low cell/low medium" (A, re-inoculated all the cells cultured for 8 hr after inoculation with a low inoculum size into medium supernatant cultured for 8 hr after inoculation with a low inoculum size);

"low cell/high medium" (B, re-inoculated all the cells cultured for 8 hr after inoculation with a low inoculum size into medium supernatant cultured for 8 hr after inoculation with a high inoculum size);

"high cell/low medium" (C, inoculated all the cells cultured for 8 hr after inoculation with a high inoculum size into medium supernatant cultured for 8 hr after inoculation with a low inoculum size);

"1/10 of high cell/low medium" (D, inoculated a 1/10 of cells cultured for 8 hr after inoculation with a high inoculum size into medium supernatant cultured for 8 hr after inoculation with low inoculum size; and "1/100 high cell/low medium" (E, inoculated 1/100 of cells cultured for 8 hr with a high inoculum size into medium cultured for 8 hr with a low inoculum size).

In the case of A and B, OD and final PHB concentration were reached at approximately 80 and 30 g/L, respectively. However, in the case of C, D, and E, not only OD was low, but also PHB was rarely accumulated. These results suggest that "capable" cells incubated for 8 hr after inoculation with a low inoculum size act as an important factor for a large amount of PHB production, regardless of medium conditions tested.

Unlike the capable cells, "incapable" cells incubated for 8 hr after inoculation with a high inoculum size lost their ability producing PHB.

From the above results, it was confirmed that PHB accumulation was due to cells themselves. So, capable cells act as an important factor for PHB accumulation and such capable cells can be obtained from cultivation with a low inoculum size. It was also confirmed that capable cells could produce PHB effectively, regardless of the conditions of medium.

Example 4

Preparation of ldh Mutant Strain

<4-1> The Relationship Between Lactate Production and PHB Production

Pyruvate, a precursor molecule for PHB production, acts as a branch point for the pathways for PHB and lactate production. When recombinant *E. coli* grows in LB/glucose/amp medium, carbon flow between the PHB and lactate production pathways can compete each other.

When a high inoculum size is applied, a large amount of lactate can be produced and pH might decline at an earlier stage compared to when a low inoculum size is applied. To test this possibility, lactate concentrations and pH of the two cultures grown in medium inoculated with low and high inoculum sizes were investigated. Precisely, LB/glucose 7%/amp medium was inoculated with each of low ($10^4$ cells/ml) and high ($10^5$ cells/ml) inoculum sizes, followed by 8 hour of cultivation. Then, lactate concentrations and pH in the medium were investigated (Table 1).

To measure lactate concentrations in two cultures, some of cell culture solution was taken for centrifugation. Supernatant was obtained and filtered with 0.2 μm filter paper. The filtered solution was analyzed by high performance liquid chromatography (HPLC). 0.1% of perchloric acid was used for moving phase. Column used was Shim-Pack 102H (Shimadzu, Japan) and RI detector (Waters Co. USA) was used for analysis.

TABLE 1

Comparison of lactate concentrations and medium pH.

| Inoculum size | Lactate (mg/l) | pH |
| --- | --- | --- |
| Low ($10^4$) | 278.57 ± 31.2 | 5.86 ± 0.20 |
| High ($10^5$) | 604.90 ± 55.6 | 4.89 ± 0.23 |

As a result, lactate concentration in medium inoculated with a high inoculum size ($10^5$ cells/ml) was two times higher than that in medium inoculated with a low inoculum size ($10^4$ cells/ml). Besides, pH dropped by 1 and hydrogen ion concentration was increased about 10 times. Therefore, the possibility was proved to be real.

<4-2> Preparation of ldh Mutant Strain Deficient in Lactate Production

Although a high inoculum size ($10^5$ cells/ml) is applied, negative effects of lactate on PHB production can be eliminated only if lactate production pathway is intercepted and pH drop is slowed down.

The present inventors constructed a new mutant strain having mutated ldh gene involved in lactate production by p1-transduction (Miller, J. H., Experiments in molecular genetics. Cold Spring Harbor Laboratory Press, Cold Spring Harbor, N.Y. 1972). In particular, JIL938 (MG1655, ldh:: Tn10) strain (referred as "JIL938" or "JIL938/pTZ18U-

PHB" hereinafter), which was deficient in lactate dehydrogenase, was constructed from wild type *E. coli* SE1752 (Bunch, P. K. *Microbiology*, 143: 187-195, 1997), an inducible strain of *E. coli* K-12.

Particularly, P1 phage containing ldh mutant was inserted into wild type strain SE1752, which was streaked onto LB medium supplemented with tetracycline. Phenotype of a colony grown in the medium was investigated to prepare JIL938, a ldh mutant strain. pTZ18U-PHB plasmid was inserted into the above mutant JIL938, which was streaked onto LB/amp agar plate. Strains grown up on the medium were recovered, resulting in a novel recombinant host strain 'JIL938/pTZ18U-PHB'.

The recombinant mutant strain was suspended in LB/20% glycerol and then stored at −80° C., just like the storage of MG1655/pTZ18U-PHB stock seed.

Figure 5:
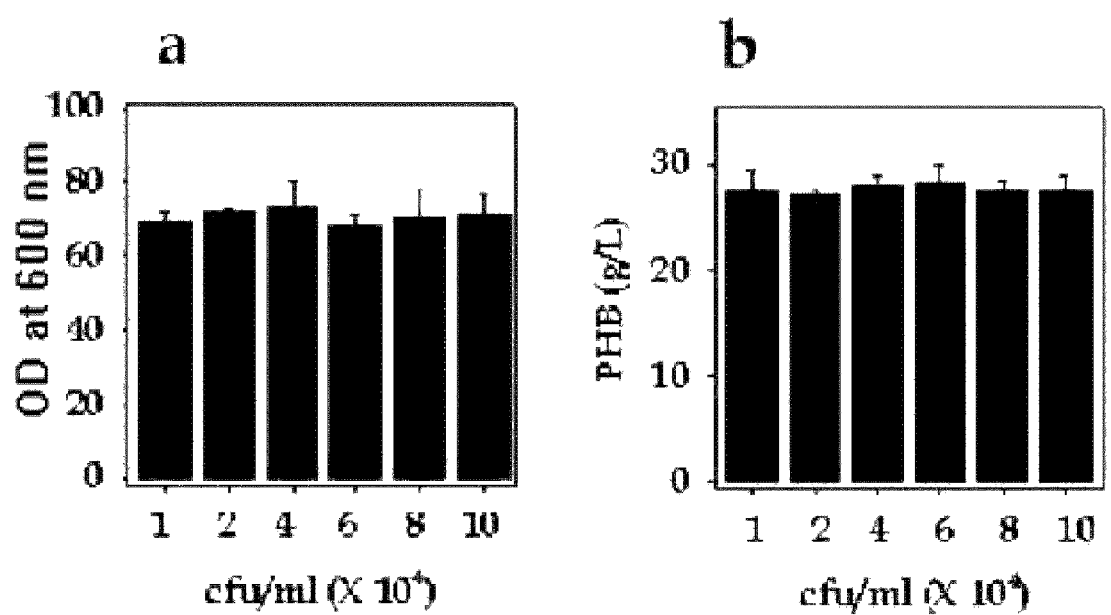
FIG. 5 is a set of graphs showing the comparison of $OD_{600}$ (left) and PHB concentration (right) according to various inoculum sizes ($10^4$~$10^5$ cells/ml). A ldh mutant strain (JIL938/pTZ18U-PHB) was inoculated in LB/glucose 7%/amp liquid medium and final $OD_{600}$ and PHB concentration were measured after incubation for 48 hours.

The recombinant ldh-deficient host strain containing pTZ18U-PHB plasmid produced PHB effectively in LB/glucose 7%/amp medium, regardless of inoculum sizes, suggesting that lactate production pathway affected PHB production negatively (FIG. 5).

Example 5

Non-Growth Dependent PHB Production

After 6-8 hour of cultivation, OD of the recombinant *E. coli* was increased although the number of viable cells remained unchanged, suggesting the possibility that the recombinant *E. coli* might produce PHB in a non-growth dependent manner (FIG. 4*b*).

In order to investigate whether or not PHB production is associated with growth, a novel plasmid pPHB-n not harboring normal phbCAB gene was prepared.

In order to prepare pPHB-n plasmid, a part of phbC obtained by digesting pTZ18U-PHB plasmid with PstI restriction enzyme and a vector devoid of a 3.38 kb long fragment containing a whole phbAB gene were connected by T4 DNA ligase.

A mutant *E. coli* strain MG1655/pPHB-n devoid of phbCAB gene was constructed using the plasmid prepared above. Precisely, MG1655 was transfected with pPHB-n plasmid and the transformant was streaked onto LB/amp agar plate. A strain growing up on the medium was selected, resulting in the preparation of MG1655/pPHB-n host strain.

The recombinant *E. coli* strain and the other strain prepared in the example <1-1> were compared. Precisely, supernatants were obtained from LB/glucose 7%/amp medium each after 4, 6 or 8 hour cultivation, into which a recombinant *E. coli* host strain (MG1655/pPHB-n) containing pPHB-n plasmid devoid of normal phbCAB gene and MG1655/pTZ18U-PHB harboring normal phbCAB gene were applied with a low inoculum size ($10^4$ cells/ml).

As a result, MG1655/pPHB-n did grow normally in the 4-hour culture medium, but it grew slowly in 6-hour culture medium and did not grow at all in the 8-hour culture medium. These results suggest that *E. coli* without phbCAB gene cannot grow normally in 8-hour culture medium. On the contrary, MG1655 carrying normal phbCAB gene can still grow in the 8-hour culture medium, indicating that PHB must be produced in a non-growth dependent manner.

The present inventors performed another experiment to prove that PHB is accumulated in a non-growth-associated manner. At first, MG1655/pTZ18U-PHB was inoculated onto LB/amp medium which was not supplemented with glucose with a low inoculum size ($10^4$ cells/ml), followed by 8-hour cultivation (FIG. 6*b*). 7% glucose was provided to the culture above. Turbidity of the culture solution became thick and PHB was effectively accumulated after glucose supplementation, meaning that cell number was increased at an early stage regardless of PHB production, and then PHB became non-growth dependently accumulated in the late stage.

As explained hereinbefore, "capable" *E. coli* cells grown in LB/glucose 7%/amp medium for 8 hours could produce PHB effectively and those cells were believed to produce PHB regardless of initial inoculum sizes. In order to prove that, MG1655/pTZ18U-PHB cells grown for 8 hours in LB/glucose 7%/amp medium were inoculated in fresh LB/glucose/amp medium with several initial inoculum sizes. As a result, PHB was effectively accumulated regardless of initial inoculum sizes (FIG. 6*c*). Similarly, when the capable cells were inoculated 1.5 times in the low medium collected from the 8-hour culture after inoculation with a low inoculum size, PHB concentration rose to nearly 40 g/l (FIG. 6*d*). These results strongly suggest that it is important for cells to obtain the capability of PHB production in early growth times (0 to 8 hr) and, if cells gain the ability, then PHB is produced in a non-growth-associated manner.

Example 6

Effects of Initial Glucose Concentration and Analysis of Multiple Parameters

The present inventors tested the effect of initial glucose concentration on PHB production.

Particularly, some of culture fluid was taken to be centrifuged to investigate glucose concentration in the medium, from which supernatant was obtained. Glucose content in the supernatant was measured by an enzymatic analysis using a glucose analysis kit (Sigma Co, 510-DA).

A recombinant *E. coli* strain MG1655/pTZ18U-PHB consumed all the glucose provided by 0~7%. About 1~3% glucose remained in the culture medium when glucose was supplied by 8~10% (FIG. 7*a*). PHB production was investigated in each case of glucose supply, resulting that PHB production was increased in proportion to glucose concentration (0% to 7%) supplied in the media (FIG. 7*b*). Interestingly, PHB content was also proportional to PHB concentrations, indicating that increased glucose concentrations led to larger obtainable amount of PHB and higher PHB content. As measured by microscopic views and viable cell counts, when glucose concentration was increased more PHB accumulated in the cell as expected, but the numbers of viable cells were similar to each other. These results suggest that the maximum glucose concentration usable by recombinant *E. coli* is 7%, and a supply below 7% leads to insufficient carbon supply, resulting in lower PHB concentration and PHB content.

A glucose supply over 7% remained unused in the medium, suggesting that the maximum glucose concentration addable to a medium for the culture of MG1655/pTZ18U-PHB strain is 7%.

The present inventors also analyzed the various important parameters affecting PHB productivity. First, the inventors investigated full profiles of OD and glucose left in the culture medium according to growth time in LB/glucose 7%/amp broth (FIG. 7*c*). Final OD reached approximately 80, and glucose provided to the medium was all consumed (7%). Dry cell weight and PHB production were also measured, and final PHB production reached 30 g/l (FIG. 7*d*). In order to measure the DCW, 1 ml of culture medium was washed twice with distilled water, followed by centrifugation. Precipitates were put in a micro-tube weighed already, and dried in 80° C. dryer for 48 hours, determining DCW.

Viable cell number was calculated; it increased up to 6 hr of cultivation, and then decreased as expected (FIG. 7e). PHB content (P/X) was calculated on the basis of DCW and PHB concentration, and reached approximately 96% (FIG. 7f). Finally, based on the extremely high level of P/X obtained, the efficiency of autolysis was determined. Autolysis was determined by comparing the β-galactosidase (referred as "β-gal" hereinafter) activities of culture medium and whole cell culture (intracellular activity plus activity in culture medium). That is, the activity of β-gal in cell culture medium was measured, and the activity of β-gal in supernatant obtained from centrifugation with the cell culture medium was measured. And the two activities were compared to determine the efficiency of autolysis.

Precisely, the activity of β-gal was measured as follows. Cell samples were added into 0.9 ml of Z-buffer ($Na_2HPO_4.7H_2O$ 16.1 g; $NaH_2PO_4.H_2O$ 5.5 g; KCl 0.75 g; $MgSO_4.7H_2O$ 0.246 g; β-mercaptoethanol 2.7 m; pH 7.0), to which 0.1% SOD and 10 μl of chloroform were added. After the supplementation, the buffer was shaken tough for 10 seconds to crush the cell samples. Then, they were suspended in 28° C. bath for 5 minutes. After adding 0.2 ml of ONPG (o-nitrophenyl-β-D-galactopyranoside), the activity of β-gal was measured. The unit was determined by following formula.

$$\text{β-gal activity (Miller unit)}=OD_{600}\times 1.75\times 1000 \div OD_{420}\times \text{Time (Min)}\times \text{Volume (ml)}$$

As a result, after 30 hr of cultivation, the cells were lysed and the proteins were extracted, and up to approximately 50% of β-galactosidase enzymes were spontaneously released outside the cells after 60 hr of incubation.

Morphologic changes of cells according to culture time were observed by optical microscope after staining with crystal violet (FIG. 8). Intracellular PHB granules remained unstained, but the size of them increased as culture time went on. Extremely high PHB content was detected after 36 hour of cultivation, and autolysis was also observed from then on.

Example 7

Maximization of PHB Yield by Controlling Medium Composition

As shown in FIG. 7a and FIG. 7b, the more glucose was supplied, the more PHB was produced. However, although glucose concentrations above 7% were provided, no additional PHB accumulated because the recombinant cells consumed a maximum of 7% glucose and extra glucose was left unused in the culture medium. This phenomenon might result from: (i) negative effect of glucose in the presence of high glucose concentration, and/or (ii) an insufficient supply or an early exhaustion of other ingredient for PHB production except glucose (e.g., some ingredients of LB). However, when a total of 10% glucose was fed intermittently to minimize the negative effect of glucose, with 7% glucose supplied at 0 hr and 3% at 24 hr, the final PHB yield was the same as that obtained with an initial supply of 7% glucose. This indicates that the upper usable limit of 7% glucose might be the result of an insufficient supply of some other ingredients rather than negative effect of glucose.

Thus, supply of necessary but unknown ingredients could promote PHB production. To prove this hypothesis, the amount of LB, being used as a basic medium, was increased, so that MG1655/pTZ18U-PHB strain was cultured in 2×LB (20 bacto-tryptone 20 g/l, bacto-yeast extract 10 g/l, NaCl 10 g/l)/glucose 7%/amp medium. Similar patterns of OD and glucose consumption were shown, comparing to the case when 1×LB/glucose 7%/amp medium was used (FIG. 9a). However, PHB content and autolysis in 2×LB/glucose 7%/amp medium were 94% and 40% respectively, which were lower than those in 1×LB/glucose 7%/amp medium (FIG. 9b). This indicates that autolysis by over-production of intracellular PHB can be delayed by sufficient supply of medium compositions, so that intracellular PHB accumulation must be greater than usual in order to increase autolysis.

Concerned about insufficient glucose supply in 2×LB/glucose 7%/amp medium, a larger amount of glucose was added. At that time, to prevent negative effect of glucose, 7% glucose was added at 36 and 60 hour of culture time, making a total of 21% glucose concentration. As a result, final OD reached up to 120 and all of the supplied glucose (total of 21%) was completely exhausted (FIG. 9c) Moreover, final DCW and PHB concentrations reached 85.5 g/l and 85.2 g/l, respectively, which were comparable to the levels achieved by fed-batch cultivation using a fermentor. After consuming all of 21% glucose, PHB content and autolysis were each 99.7% and 80%, indicating that intracellular PHB was highly accumulated by a large amount of glucose and intracellular PHB granules were effectively autolyzed outside cells into the medium by cell destruction resulted from a huge amount of accumulated PHB (FIG. 9d). From the observation under optical microscope, it was confirmed that the size of cells grown in 2×LB medium was bigger than that cultured in 1×LB medium, resulted from the supply of sufficient medium and glucose, and cells were filled with PHB almost 100% (FIG. 10a and FIG. 10b).

MG1655/pPHB-n grown in 1×LB/glucose 7%/amp (1), and MG1655/pTZ18U-PHB cells grown in 1×LB/glucose 7%/amp (2), 2×LB/glucose 7%/amp (3), and 2×LB/glucose 21% (total amount supplied)/amp (4) were photographed after washing with distilled water one time and drying for 48 hr at 80° C. While MG1655/pPHB-n, which could not accumulate intracellular PHB due to the lack of phbCAB genes, showed dark-brown color, MG1655/pTZ18U-PHB cells grown in 1×LB/glucose 7%/amp and containing 96% PHB content showed light-brown color, and MG1655/pTZ18U-PHB cells grown in 2×LB/glucose 7%/amp containing 94% PHB content showed brown color, indicating that the PHB content of cells grown in 2×LB without further glucose supplementation was lower than that of cells grown in 1×LB. Cells grown in 2×LB/glucose 21%/amp and containing 99.7% PHB content showed white-opaque color, indicating that the most intracellular portion of recombinant E. coli was filled with PHB and a large amount of PHB was released outside the cells (FIG. 10c). These results indicate that recombinant E. coli grown in 2×LB/glucose 21%/amp after inoculation with low inoculum size not only accumulates PHB at an extremely high level, but also spontaneously releases up to 80% PHB outside the cell, causing an efficiency of recovery/purification.

MG1655/pTZ18U-PHB cells grown in 2×LB/glucose 21%/amp medium were observed under scanning (SEM, FIG. 11) and transmission electron microscope (TEM, FIGS. 12a and 12b).

For that purpose, cell culture medium containing PHB granules was fixed with 2.5% (v/v) glutaraldehyde containing 2.5% paraformaldehyde, followed by fixation again with 1% osmium tetroxide. In order to dehydrate the sample, ethanol was treated to it degree by degree. In particular, images of the sample were captured by scanning electron microscope (JSM6300 SEM, JEOL Ltd. Japan) after coating it with gold. For the observation under transmission electron microscope, samples were driven in Epon 812, leading to making sections of them by using LKB2008 Ultratome V. Thin sections (80 nm in thick) were put on 200 mesh grid and observed with energy-filtering TEM (120 kV EM912 Omega, Carl Zeiss Co. Germany).

As shown in FIG. 11, cells were filled with PHB granules (a), and intracellular PHB granules were released outside the cells through the open cell membrane (b, arrow).

Such phenomenon was well observed under TEM. In conclusion, cells were filled with PHB granules (FIG. 12a) and PHB granules were effectively released outside the cells through the open cell membrane broken by over-accumulation of PHB granules (FIG. 12b, arrow).

INDUSTRIAL APPLICABILITY

As explained hereinbefore, the method of the present invention not only facilitates an overproduction of polyhydroxyalkanoate such as polyhydroxybutyrate by a simple batch-culture but also provides simple and easy recovery/purification processes based on high polyhydroxyalkanoate content. In addition to simplifying the process of fermentation, glucose can be efficiently converted into polyhydroxyalkanoate by the method of the present invention. The method of the present invention also facilitates an industrial use of biodegradable polyhydroxyalkanoate replacing conventional non-biodegradable plastics.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

What is claimed is:

1. A method for overproducing polyhydroxyalkanoate comprising:
   i) preparing transformed *Escherichia coli* comprising a phbCAB genes originated from *Alcaligenes eutrophus*, wherein the *Escherichia coli* is not ldh deficient;
   ii) seed-culturing the transformed *Escherichia coli*;
   iii) inoculating LB culture medium with cells resulting from the seed culture of step ii) to contain less than $2 \times 10^4$ cells per ml in the LB culture medium, and culturing the cells through growth phase;
   iv) producing the polyhydroxyalkanoate in the cultured cells during stationary phase;
   v) secreting the polyhydroxyalkanoate extracellularly from the cultured cells; and
   vi) purifying the polyhydroxyalkanoate,
   wherein the phbCAB genes comprises a phbC gene having the nucleotide sequence of SEQ ID NO: 1, a phbA gene having the nucleotide sequence of SEQ ID NO: 2 and a phbB gene having the nucleotide sequence of SEQ ID NO:3, fused from 5' to 3' in the order given, and
   glucose is added to the LB medium during the growth and/or the stationary phase such that the glucose concentration in the LB culture medium is less than 10%, w/v, immediately after adding the glucose.

2. The method as set forth in claim 1, wherein the glucose is added during the stationary phase.

3. The method as set forth in claim 1, wherein the glucose concentration in the LB culture medium is less than 7%, w/v, immediately after adding the glucose.

4. The method as set forth in claim 3, wherein the LB medium further comprises ampicillin.

5. The method as set forth in claim 1, wherein the polyhydroxyalkanoate is polyhydroxybutyrate (PHB).

6. The method as set forth in claim 1, wherein the LB medium is composed of at least 10 g of Bacto tryptone, at least 5 g of Bacto-yeast extract and at least 10 g of NaCl per liter.

7. The method as set forth in claim 6, wherein the LB medium is composed of 10-20 g of Bacto-tryptone, 5-10 g of Bacto-yeast extract and 10-20 g of NaCl per liter.

8. The method of claim 2, wherein the glucose concentration in the LB culture medium is less than or equal to 7%, w/v, immediately after adding the glucose.

9. The method of claim 2, wherein the glucose is added when the LB medium comprises a glucose concentration of 0.01 g/liter or less.

10. The method of claim 2, wherein the glucose concentration in the LB culture medium is less than or equal to 7%, w/v, immediately after adding the glucose twice.

11. The method as set forth in claim 1, wherein the glucose is added during the growth phase.

12. The method of claim 11, wherein the transformed *Escherichia coli* are cultured in a simple batch culture after the glucose is added.

* * * * *